(12) United States Patent
Gearing

(10) Patent No.: US 9,580,496 B2
(45) Date of Patent: *Feb. 28, 2017

(54) THERAPEUTIC CANINE IMMUNOGLOBULINS AND METHODS OF USING SAME

(75) Inventor: David Gearing, Southbank (AU)

(73) Assignee: NEXVET AUSTRALIA PTY LTD, Melbourne, Victoria (AU)

(*) Notice: Subject to any disclaimer, the term of this patent is extended or adjusted under 35 U.S.C. 154(b) by 468 days.

This patent is subject to a terminal disclaimer.

(21) Appl. No.: 14/115,779

(22) PCT Filed: May 8, 2012

(86) PCT No.: PCT/GB2012/051008
§ 371 (c)(1),
(2), (4) Date: Feb. 6, 2014

(87) PCT Pub. No.: WO2012/153126
PCT Pub. Date: Nov. 15, 2012

(65) Prior Publication Data
US 2014/0170137 A1 Jun. 19, 2014
US 2015/0056183 A9 Feb. 26, 2015

Related U.S. Application Data

(60) Provisional application No. 61/483,481, filed on May 6, 2011, provisional application No. 61/531,439, filed on Sep. 6, 2011.

(30) Foreign Application Priority Data

Aug. 29, 2011 (GB) .................................. 1114858.2

(51) Int. Cl.
*C07K 16/22* (2006.01)
*C07K 16/28* (2006.01)
*C07K 1/16* (2006.01)
*A61K 39/00* (2006.01)

(52) U.S. Cl.
CPC .............. *C07K 16/22* (2013.01); *C07K 1/165* (2013.01); *C07K 16/2887* (2013.01); *A61K 2039/505* (2013.01); *C07K 2317/24* (2013.01); *C07K 2317/41* (2013.01); *C07K 2317/70* (2013.01); *C07K 2317/76* (2013.01); *C07K 2317/92* (2013.01); *C07K 2319/00* (2013.01)

(58) Field of Classification Search
None
See application file for complete search history.

(56) References Cited

U.S. PATENT DOCUMENTS 6,703,360 B2 * 3/2004 McCall .............. C07K 14/7155 424/192.1
8,680,237 B2 * 3/2014 Strome ................. C07K 16/00 530/350
9,328,164 B2   5/2016 Gearing

FOREIGN PATENT DOCUMENTS

FOREIGN PATENT DOCUMENTS

| EP | 2 138 512 B1 | 12/2009 | |
|---|---|---|---|
| WO | WO-93/16192 | 8/1993 | |
| WO | WO-01/77332 | 10/2001 | |
| WO | WO 0177332 A2 * | 10/2001 | ......... C07K 14/7155 |
| WO | WO-03/002607 A1 | 1/2003 | |
| WO | WO-03/060080 | 7/2003 | |
| WO | WO-2004/020579 A2 | 3/2004 | |
| WO | WO-2005/061540 | 7/2005 | |
| WO | WO-2006/131951 A2 | 12/2006 | |
| WO | WO-2010/027488 A2 | 3/2010 | |
| WO | WO-2010/110838 A2 | 9/2010 | |
| WO | WO-2010/117448 A2 | 10/2010 | |
| WO | WO 2010117448 A2 * | 10/2010 | ............ C07K 14/52 |
| WO | WO-2012/024650 A2 | 2/2012 | |

OTHER PUBLICATIONS

Janeway et al., Immunobiology, 3$^{rd}$ edition 1997, Garland Publishing Inc, pp. 3:1-3:11.*
Rudikoff et al., Proc Natl Acad Sci U S A. Mar. 1982;79(6):1979-83.*
Fundamental Immunology, William E. Paul, M.D. ed., 3d ed. 1993, p. 242.*
Portolano et al., J Immunol. Feb. 1, 1993;150(3):880-7.*
Fior et al., Eur Cytokine Netw. Nov.-Dec. 1994;5(6):593-600.*
Liu et al., "Recovery and purification process development for monoclonal antibody production," mAbs, vol. 2, Issue 5, pp. 480-499, Sep./Oct. 2010.
Gorman and Clark, "Humanisation of monoclonal antibodies for therapy," Seminars in Immunology, vol. 2, pp. 457-466, Nov. 1990.
Gorman et al., "Reshaping a therapeutic CD4 antibody," Proc. Natl. Acad. Sci USA, vol. 88, pp. 4181-4185, May 1991.
Riechmann et al., "Reshaping human antibodies for therapy," Nature, vol. 332, pp. 323-327, Mar. 1988.
U.S. Appl. No. 14/115,772, filed Feb. 5, 2014, David Gearing.
U.S. Appl. No. 14/115,784, filed Nov. 5, 2013, David Gearing.
U.S. Appl. No. 14/115,787, filed Feb. 11, 2014, David Gearing.
U.S. Appl. No. 14/241,616, filed Feb. 27, 2014, David Gearing.
U.S. Appl. No. 14/342,943, filed Mar. 5, 2014, David Gearing.
Abe et al., "Protective Role of Nerve Growth Factor Against Postischemic Dysfunction of Sympathetic Coronary Innervation," Circulation, vol. 95, No. 1, Jan. 7, 1997.
Cattaneo et al., "Humanized alpha D11 antibody heavy chain variable region SEQ ID No. 17," Database Accession No. AEB12537, Sep. 8, 2005.

(Continued)

*Primary Examiner* — Michael Szperka
(74) *Attorney, Agent, or Firm* — Foley & Lardner LLP

(57) ABSTRACT

A method of preparing a canine antibody suitable for use in the therapeutic treatment of a canine is provided. In particular, there is provided immunoglobulins which can be selected for the characteristic of whether they mediate downstream complement mediated immune activation when bound to a target antigen. Canine derived antibodies comprising specific heavy chain isotypes are provided. The invention extends to the use of the immunoglobulins of the invention in methods of treating conditions such as pain, inflammatory conditions and cancerous conditions in a canine.

11 Claims, 14 Drawing Sheets

(56) References Cited

OTHER PUBLICATIONS

Cattaneo, "Method for the humanization of antibodies and humanized antibodies thereby obtained Patent No. WO2005/061540-A2," Database Accesion No. CS126835, Jul. 20, 2005.
Covaceuszach et al., "Dissecting NGF Interactions with TrkA and p75 Receptors by Structural and Functional Studies of an Anti-NGF Neutralizing Antibody," Journal of Molecular Biology, Academic Press, vol. 381, No. 4, Sep. 12, 2008.
International Search Report mailed Aug. 1, 2012 issued in connection with International Application No. PCT/GB2012/051008.
International Search Report mailed Aug. 20, 2012 issued in connection with International Application No. PCT/GB2012/051004.
International Search Report mailed Aug. 30, 2012 issued in connection with International Application No. PCT/GB2012/051003.
International Search Report mailed Sep. 4, 2012 issued in connection with International Application No. PCT/GB2012/051002.
International Search Report mailed Dec. 3, 2012 issued in connection with International Application No. PCT/GB2012/052115.
International Search Report mailed Dec. 4, 2012 issued in connection with International Application No. PCT/GB2012/052174.
Karampetsou et al., "TNF-α antagonists beyond approved indications: stories of success and prospects for the future", QJM, vol. 103, No. 12, pp. 917-928, Aug. 27, 2010.
Pelat et al., "Non-human primate immune libraries combined with germline humanization: an (almost) new, and powerful approach for the isolation of therapeutic antibodies," mAbs, vol. 1, No. 4, pp. 377-381, Jul. 1, 2009.
Pelat et al., "Obtention and engineering of non-human primate (NHP) antibodies for therapeutics," Mini Reviews in Medicinal Chemistry, vol. 9, No. 14, pp. 1633-1638, Dec. 1, 2009.
Presta, "Engineering of therapeutic antibodies to minimize immunogenicity and optimize function," Advanced Drug Delivery Reviews, Elsevier vol. 58, No. 5-6, pp. 640-656, Aug. 7, 2006.
Brorson et al., "Mutational Analysis of Avidity and Fine Specificity of Anti-Levan Antibodies", J. Immunol., 163:6694-6701, Dec. 1999.
Brummell et al., "Probing the combining site of anti-carbohydrate antibody by saturation-mutagenesis: role of the heavy-chain CDR3 residues", Biochemistry, 32:1180-1187, Feb. 1993 (Abstract).
Burks et al., "In vitro scanning saturation mutagenesis of an antibody binding pocket", Proc. Natl. Acad. Sci. USA, 94:412-417, Jan. 1997.
Casset et al, "A peptide mimetic of an anti-CD4 monoclonal antibody by rational design", Biochemical and Biophysical Research Communications, 307:198-205, Jul. 2003.
Chen et al., "Selection and Analysis of an Optimized Anti-VEGF Antibody: Crystal Structure of an Affinity-matured Fab in Complex with Antigen", J. Mol. Biol., 293:865-881, Nov. 1999.
Colman, "Effects of amino acid sequence changes on antibody-antigen interactions", Research in Immunol., 145:33-36, Jan. 1994.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody", J. Immunol., 169:3076-3084, Sep. 2002.
Holm et al., "Functional mapping and single chain construction of the anti-cytokeratin 8 monoclonal antibody TS1", Molecular Immunology, 44:1075-1084, Feb. 2007.
Jang et al., "The structural basis for DNA binding by an anti-DNA autoantibody", Molecular Immunology, 35:1207-1217, Dec. 1998.
Kobayashi et al., "Tryptophan H33 plays an important role in pyrimidine (6-4) pyrimidone photoproduct binding by a high-affinity antibody", Protein Engineering, 12:879-884, Oct. 1999.
MacCallum et al., "Antibody-antigen Interactions: Contact Analysis and Binding Site Topography", J. Mol. Biol., 262:732-745, Oct. 1996.
Office action dated Jun. 9, 2015 issued in U.S. Appl. No. 14/115,787.
Rudikoff et al., "Single amino acid substitution altering antigen-binding specificity", Proc. Natl. Acad. Sci. USA, 79:1979-1983, Mar. 1982.
Vajdos et al., "Comprehensive Functional Maps of the Antigen-binding Site of an Anti-ErbB2 Antibody Obtained with Shotgun Scanning Mutagenesis", J. Mol. Biol., 320:415-428, Jul. 2002.
Wu et al, "Humanization of a Murine Antibody by Simultaneous Optimization of Framework and CDR Residues", J. Mol. Biol. 294:151-162, Nov. 1999.
Tang et al., "Cloning and characterization of cDNAs encoding four different canine immunoglobulin γ chains", Vet. Immunol. Immunopathol., 80:259-270, Aug. 2001.
NCBI Genbank Accession No. AAA61986, "NGF-binding Ig light chain; partial [Rattus norvegicus]," Feb. 7, 1995.
NCBI Genbank Accession No. AAA61985, "NGF-binding Ig heavy chain, partial [Rattus norvegicus]," Feb. 7, 1995.
Wagner et al., "A monoclonal antibody to equine interleukin-4," Veterinary Immunology and Immunopathology, vol. 110, pp. 363-367, Feb. 2006.
Foote et al., "Antibody Framework Residues Affecting the Conformation of the Hypervariable Loops," J. Mol. Biol., vol. 224, pp. 487-490, Mar. 1992.
Office Action issued on Apr. 13, 2016 in U.S. Appl. No. 14/115,784 (U.S. Pat. No. 2015-0017154).
Office Action issued on Jan. 29, 2016 in U.S. Appl. No. 14/342,943 (U.S. Pat. No. 2014-0328838).
Office Action issued on May 20, 2016 in U.S. Appl. No. 14/115,772 (U.S. Pat. No. 2014-0170136).
Office Action issued on Nov. 27, 2015 in U.S. Appl. No. 14/115,772 (U.S. Pat. No. 2014-0170136).
Notice of Allowance issued on Dec. 31, 2015 in U.S. Appl. No. 14/115,787 (U.S. Pat. No. 9,328,164).
Office Action issued on Jun. 9, 2015 in U.S. Appl. No. 14/115,787 (U.S. Pat. No. 9,328,164).

* cited by examiner

| Peak Retention time (Mins) | Approximate MW (KDa) | % of Total Peak area |
|---|---|---|
| 8.05 | 353 | 2.6 |
| 9.17 | 156 | 89.7 |
| 11.18 | 36 | 7.7 |

SDS-PAGE

Non-Reducing

Mouse MAb | NV-01
I  II 230
150
100
80
60
50
40
30
25

Reducing

Mouse MAb | NV-01
I  II 230
150
100
80
60
50
40
30
25

Figure 7A

| Study Day | | | -1 | 1 | 3 | 7 |
|---|---|---|---|---|---|---|
| Animal ID | Sex | Age on Study Day 0 (months) | | | | |
| 68305 | M | 11 | 9.6 | 10.0 | 9.9 | 10.0 |
| 26885 | F | 19 | 9.2 | 9.9 | 9.5 | 9.8 |
| 32886 | F | 11 | 9.4 | 9.9 | 9.7 | 10.0 |

| Study Day | 0 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|
| Animal ID | | | | | | | | | | | | | | | |
| 68305 | 38.2 | 38.6 | 38.6 | 38.5 | 38.4 | 38.5 | 38.4 | 38.3 | 38.7 | 38.2 | 38.3 | 38.9 | 38.4 | 38.6 | 38.5 |
| 26886 | 37.8 | 38.2 | 38.0 | 38.2 | 38.4 | 37.7 | 38.1 | 38.2 | 38.4 | 38.2 | 38.4 | 38.6 | 38.5 | 38.4 | 38.6 |
| 32886 | 36.8 | 38.7 | 38.9 | 38.8 | 38.7 | 38.8 | 38.7 | 38.5 | 38.8 | 38.7 | 38.3 | 39.2 | 38.7 | 38.7 | 38.8 |

Figure 8

```
                       SEQUENCE LISTING

<160> NUMBER OF SEQ ID NOS: 15

<210> SEQ ID NO 1
<211> LENGTH: 453
<212> TYPE: PRT
<213> ORGANISM: Artificial Sequence
<220> FEATURE:
<223> OTHER INFORMATION: Caninised anti-NGF VH canine IgG-A heavy chain
      (caN-HCA)

<400> SEQUENCE: 1

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu His Ser Leu Ser Ser Met Val Thr
            180                 185                 190

Val Pro Ser Ser Arg Trp Pro Ser Glu Thr Phe Thr Cys Asn Val Val
        195                 200                 205
```

His Pro Ala Ser Asn Thr Lys Val Asp Lys Pro Val Phe Asn Glu Cys
    210                 215                 220
Arg Cys Thr Asp Thr Pro Cys Pro Val Pro Glu Pro Leu Gly Gly
225                 230                 235                 240
Pro Ser Val Leu Ile Phe Pro Lys Pro Lys Asp Ile Leu Arg Ile
                    245                 250                 255
Thr Arg Thr Pro Glu Val Thr Cys Val Val Leu Asp Leu Gly Arg Glu
                260                 265                 270
Asp Pro Glu Val Gln Ile Ser Trp Phe Val Asp Gly Lys Glu Val His
            275                 280                 285
Thr Ala Lys Thr Gln Ser Arg Glu Gln Gln Phe Asn Gly Thr Tyr Arg
        290                 295                 300
Val Val Ser Val Leu Pro Ile Glu His Gln Asp Trp Leu Thr Gly Lys
305                 310                 315                 320
Glu Phe Lys Cys Arg Val Asn His Ile Asp Leu Pro Ser Pro Ile Glu
                325                 330                 335
Arg Thr Ile Ser Lys Ala Arg Gly Arg Ala His Lys Pro Ser Val Tyr
                340                 345                 350
Val Leu Pro Pro Ser Pro Lys Glu Leu Ser Ser Ser Asp Thr Val Ser
            355                 360                 365
Ile Thr Cys Leu Ile Lys Asp Phe Tyr Pro Pro Asp Ile Asp Val Glu
        370                 375                 380
Trp Gln Ser Asn Gly Gln Gln Glu Pro Glu Arg Lys His Arg Met Thr
385                 390                 395                 400
Pro Pro Gln Leu Asp Glu Asp Gly Ser Tyr Phe Leu Tyr Ser Lys Leu
                405                 410                 415
Ser Val Asp Lys Ser Arg Trp Gln Gln Gly Asp Pro Phe Thr Cys Ala
                420                 425                 430
Val Met His Glu Thr Leu Gln Asn His Tyr Thr Asp Leu Ser Leu Ser
            435                 440                 445
His Ser Pro Gly Lys
    450

<210> SEQ ID NO 2
<211> LENGTH: 457
<212> TYPE: PRT
<213> ORGANISM: Artificial Sequence
<220> FEATURE:
<223> OTHER INFORMATION: Caninised anti-NGF VH canine IgG-B heavy chain
      (caN-HCB)

<400> SEQUENCE: 2

Glu Val Gln Leu Val Glu Ser Gly Gly Asp Leu Val Asn Pro Gly Gly
1               5                   10                  15
Thr Leu Thr Leu Ser Cys Val Val Ser Gly Phe Ser Leu Thr Asn Asn
                20                  25                  30
Asn Val Asn Trp Val Arg Gln Ala Leu Gly Arg Gly Leu Glu Trp Val
            35                  40                  45
Gly Gly Val Trp Ala Gly Gly Ala Thr Asp Tyr Asn Ser Ala Leu Lys
        50                  55                  60
Ser Arg Leu Thr Ile Thr Arg Asp Thr Ser Lys Ser Thr Val Phe Leu
65                  70                  75                  80
Lys Met His Ser Leu Gln Ser Glu Asp Thr Ala Thr Tyr Tyr Cys Ala
                85                  90                  95
Arg Asp Gly Gly Tyr Ser Ser Ser Thr Leu Tyr Ala Met Asp Ala Trp

```
              100                 105                 110
Gly Gln Gly Thr Leu Val Thr Val Ser Ser Ala Ser Thr Thr Ala Pro
            115                 120                 125
Ser Val Phe Pro Leu Ala Pro Ser Cys Gly Ser Thr Ser Gly Ser Thr
        130                 135                 140
Val Ala Leu Ala Cys Leu Val Ser Gly Tyr Phe Pro Glu Pro Val Thr
145                 150                 155                 160
Val Ser Trp Asn Ser Gly Ser Leu Thr Ser Gly Val His Thr Phe Pro
                165                 170                 175
Ser Val Leu Gln Ser Ser Gly Leu Tyr Ser Leu Ser Ser Met Val Thr
            180                 185                 190
Val Pro Ser Ser Arg Trp Pro Ser Glu Thr Phe Thr Cys Asn Val Ala
        195                 200                 205
His Pro Ala Ser Lys Thr Lys Val Asp Lys Pro Val Pro Lys Arg Glu
    210                 215                 220
Asn Gly Arg Val Pro Arg Pro Asp Cys Pro Lys Cys Pro Ala Pro
225                 230                 235                 240
Glu Met Leu Gly Gly Pro Ser Val Phe Ile Phe Pro Pro Lys Pro Lys
                245                 250                 255
Asp Thr Leu Leu Ile Ala Arg Thr Pro Glu Val Thr Cys Val Val Val
            260                 265                 270
Asp Leu Asp Pro Glu Asp Pro Glu Val Gln Ile Ser Trp Phe Val Asp
        275                 280                 285
Gly Lys Gln Met Gln Thr Ala Lys Thr Gln Pro Arg Glu Glu Gln Phe
    290                 295                 300
Asn Gly Thr Tyr Arg Val Val Ser Val Leu Pro Ile Gly His Gln Asp
305                 310                 315                 320
Trp Leu Lys Gly Lys Gln Phe Thr Cys Lys Val Asn Asn Lys Ala Leu
                325                 330                 335
Pro Ser Pro Ile Glu Arg Thr Ile Ser Lys Ala Arg Gly Gln Ala His
            340                 345                 350
Gln Pro Ser Val Tyr Val Leu Pro Pro Ser Arg Glu Glu Leu Ser Lys
        355                 360                 365
Asn Thr Val Ser Leu Thr Cys Leu Ile Lys Asp Phe Tyr Pro Pro Asp
    370                 375                 380
Ile Asp Val Glu Trp Gln Ser Asn Gly Gln Gln Glu Pro Glu Ser Lys
385                 390                 395                 400
Tyr Arg Thr Thr Pro Pro Gln Leu Asp Glu Asp Gly Ser Tyr Phe Leu
                405                 410                 415
Tyr Ser Lys Leu Ser Val Asp Lys Ser Arg Trp Gln Arg Gly Asp Thr
            420                 425                 430
Phe Ile Cys Ala Val Met His Glu Ala Leu His Asn His Tyr Thr Gln
        435                 440                 445
Glu Ser Leu Ser His Ser Pro Gly Lys
    450                 455

<210> SEQ ID NO 3
<211> LENGTH: 455
<212> TYPE: PRT
<213> ORGANISM: Artificial Sequence
<220> FEATURE:
<223> OTHER INFORMATION: Caninised anti-NGF VH canine IgG-C heavy chain
      (caN-HCC)

<400> SEQUENCE: 3
```

-continued

```
Glu Val Gln Leu Val Glu Ser Gly Gly Asp Leu Val Asn Pro Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Val Trp Ala Gly Gly Ala Thr Asp Tyr Asn Ser Ala Leu Lys
50                  55                  60

Ser Arg Leu Thr Ile Thr Arg Asp Thr Ser Lys Ser Thr Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Thr Leu Tyr Ala Met Asp Ala Trp
            100                 105                 110

Gly Gln Gly Thr Leu Val Thr Val Ser Ser Ala Ser Thr Thr Ala Pro
                115                 120                 125

Ser Val Phe Pro Leu Ala Pro Ser Cys Gly Ser Gln Ser Gly Ser Thr
    130                 135                 140

Val Ala Leu Ala Cys Leu Val Ser Gly Tyr Ile Pro Glu Pro Val Thr
145                 150                 155                 160

Val Ser Trp Asn Ser Val Ser Leu Thr Ser Gly Val His Thr Phe Pro
            165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Thr Asn Thr Lys Val Asp Lys Pro Val Ala Lys Glu Cys
    210                 215                 220

Glu Cys Lys Cys Asn Cys Asn Asn Cys Pro Cys Pro Gly Cys Gly Leu
225                 230                 235                 240

Leu Gly Gly Pro Ser Val Phe Ile Phe Pro Pro Lys Pro Lys Asp Ile
            245                 250                 255

Leu Val Thr Ala Arg Thr Pro Thr Val Thr Cys Val Val Val Asp Leu
            260                 265                 270

Asp Pro Glu Asn Pro Glu Val Gln Ile Ser Trp Phe Val Asp Ser Lys
    275                 280                 285

Gln Val Gln Thr Ala Asn Thr Gln Pro Arg Glu Glu Gln Ser Asn Gly
    290                 295                 300

Thr Tyr Arg Val Val Ser Val Leu Pro Ile Gly His Gln Asp Trp Leu
305                 310                 315                 320

Ser Gly Lys Gln Phe Lys Cys Lys Val Asn Asn Lys Ala Leu Pro Ser
                325                 330                 335

Pro Ile Glu Glu Ile Ile Ser Lys Thr Pro Gly Gln Ala His Gln Pro
            340                 345                 350

Asn Val Tyr Val Leu Pro Pro Ser Arg Asp Glu Met Ser Lys Asn Thr
            355                 360                 365

Val Thr Leu Thr Cys Leu Val Lys Asp Phe Phe Pro Pro Glu Ile Asp
    370                 375                 380

Val Glu Trp Gln Ser Asn Gly Gln Gln Glu Pro Glu Ser Lys Tyr Arg
385                 390                 395                 400

Met Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
```

```
                420                 425                 430
Cys Ala Val Met His Glu Ala Leu His Asn His Tyr Thr Gln Ile Ser
                435                 440                 445

Leu Ser His Ser Pro Gly Lys
        450                 455

<210> SEQ ID NO 4
<211> LENGTH: 453
<212> TYPE: PRT
<213> ORGANISM: Artificial Sequence
<220> FEATURE:
<223> OTHER INFORMATION: Caninised anti-NGF VH canine IgG-D heavy chain
      (caN-HCD)

<400> SEQUENCE: 4

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
                20                  25                  30

Asn Val Asn Trp Val Arg Gln Ala Leu Gly Arg Gly Leu Glu Trp Val
                35                  40                  45

Gly Gly Val Trp Ala Gly Gly Ala Thr Asp Tyr Asn Ser Ala Leu Lys
        50                  55                  60

Ser Arg Leu Thr Ile Thr Arg Asp Thr Ser Lys Ser Thr Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Thr Leu Tyr Ala Met Asp Ala Trp
                100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
        130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Thr Val Thr
                180                 185                 190

Val Pro Ser Ser Arg Trp Pro Ser Glu Thr Phe Thr Cys Asn Val Val
                195                 200                 205

His Pro Ala Ser Asn Thr Lys Val Asp Lys Pro Val Pro Lys Glu Ser
        210                 215                 220

Thr Cys Lys Cys Ile Ser Pro Cys Pro Val Pro Glu Ser Leu Gly Gly
225                 230                 235                 240

Pro Ser Val Phe Ile Phe Pro Pro Lys Pro Lys Asp Ile Leu Arg Ile
                245                 250                 255

Thr Arg Thr Pro Glu Ile Thr Cys Val Val Leu Asp Leu Gly Arg Glu
                260                 265                 270

Asp Pro Glu Val Gln Ile Ser Trp Phe Val Asp Gly Lys Glu Val His
                275                 280                 285

Thr Ala Lys Thr Gln Pro Arg Glu Gln Gln Phe Asn Ser Thr Tyr Arg
        290                 295                 300

Val Val Ser Val Leu Pro Ile Glu His Gln Asp Trp Leu Thr Gly Lys
305                 310                 315                 320
```

-continued

```
Glu Phe Lys Cys Arg Val Asn His Ile Gly Leu Pro Ser Pro Ile Glu
            325                 330                 335

Arg Thr Ile Ser Lys Ala Arg Gly Gln Ala His Gln Pro Ser Val Tyr
        340                 345                 350

Val Leu Pro Pro Ser Pro Lys Glu Leu Ser Ser Ser Asp Thr Val Thr
            355                 360                 365

Leu Thr Cys Leu Ile Lys Asp Phe Tyr Pro Pro Glu Ile Asp Val Glu
370                 375                 380

Trp Gln Ser Asn Gly Gln Pro Glu Pro Glu Ser Lys Tyr His Thr Thr
385                 390                 395                 400

Ala Pro Gln Leu Asp Glu Asp Gly Ser Tyr Phe Leu Tyr Ser Lys Leu
            405                 410                 415

Ser Val Asp Lys Ser Arg Trp Gln Gln Gly Asp Thr Phe Thr Cys Ala
            420                 425                 430

Val Met His Glu Ala Leu Gln Asn His Tyr Thr Asp Leu Ser Leu Ser
            435                 440                 445

His Ser Pro Gly Lys
            450

<210> SEQ ID NO 5
<211> LENGTH: 217
<212> TYPE: PRT
<213> ORGANISM: Artificial Sequence
<220> FEATURE:
<223> OTHER INFORMATION: Caninised anti-NGF VL canine kappa light chain
      (caN-kLC)

<400> SEQUENCE: 5

Asp Ile Gln Met Thr Gln Ser Pro Ala Ser Leu Ser Leu Ser Gln Glu
1               5                   10                  15

Glu Lys Val Thr Ile Thr Cys Arg Ala Ser Glu Asp Ile Tyr Asn Ala
            20                  25                  30

Leu Ala Trp Tyr Gln Gln Lys Pro Gly Gln Ala Pro Lys Leu Leu Ile
        35                  40                  45

Tyr Asn Thr Asp Thr Leu His Thr Gly Val Pro Ser Arg Phe Ser Gly
    50                  55                  60

Ser Gly Ser Gly Thr Glu Tyr Ser Leu Thr Ile Asn Ser Leu Glu Ser
65                  70                  75                  80

Glu Asp Val Ala Val Tyr Phe Cys Gln His Tyr Phe His Tyr Pro Arg
            85                  90                  95

Thr Phe Gly Ala Gly Thr Lys Val Glu Leu Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
            165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215
```

<210> SEQ ID NO 6
<211> LENGTH: 457
<212> TYPE: PRT
<213> ORGANISM: Artificial Sequence
<220> FEATURE:
<223> OTHER INFORMATION: Caninised anti-NGF VH Aglycosyl canine immunoglobulin heavy chain type B (caN-HCB*)

<400> SEQUENCE: 6

```
Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Thr Ser Gly Ser Thr
    130                 135                 140

Val Ala Leu Ala Cys Leu Val Ser Gly Tyr Phe Pro Glu Pro Val Thr
145                 150                 155                 160

Val Ser Trp Asn Ser Gly Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Ser Lys Thr Lys Val Asp Lys Pro Val Pro Lys Arg Glu
    210                 215                 220

Asn Gly Arg Val Pro Arg Pro Pro Asp Cys Pro Lys Cys Pro Ala Pro
225                 230                 235                 240

Glu Met Leu Gly Gly Pro Ser Val Phe Ile Phe Pro Pro Lys Pro Lys
                245                 250                 255

Asp Thr Leu Leu Ile Ala Arg Thr Pro Glu Val Thr Cys Val Val Val
            260                 265                 270

Asp Leu Asp Pro Glu Asp Pro Glu Val Gln Ile Ser Trp Phe Val Asp
        275                 280                 285

Gly Lys Gln Met Gln Thr Ala Lys Thr Gln Pro Arg Glu Glu Gln Phe
    290                 295                 300

Ala Gly Thr Tyr Arg Val Val Ser Val Leu Pro Ile Gly His Gln Asp
305                 310                 315                 320

Trp Leu Lys Gly Lys Gln Phe Thr Cys Lys Val Asn Asn Lys Ala Leu
                325                 330                 335

Pro Ser Pro Ile Glu Arg Thr Ile Ser Lys Ala Arg Gly Gln Ala His
            340                 345                 350

Gln Pro Ser Val Tyr Val Leu Pro Pro Ser Arg Glu Glu Leu Ser Lys
```

```
              355                 360                 365
Asn Thr Val Ser Leu Thr Cys Leu Ile Lys Asp Phe Tyr Pro Pro Asp
    370                 375                 380

Ile Asp Val Glu Trp Gln Ser Asn Gly Gln Gln Pro Glu Ser Lys
385                 390                 395                 400

Tyr Arg Thr Thr Pro Gln Leu Asp Glu Asp Gly Ser Tyr Phe Leu
                405                 410                 415

Tyr Ser Lys Leu Ser Val Asp Lys Ser Arg Trp Gln Arg Gly Asp Thr
            420                 425                 430

Phe Ile Cys Ala Val Met His Glu Ala Leu His Asn His Tyr Thr Gln
            435                 440                 445

Glu Ser Leu Ser His Ser Pro Gly Lys
    450                 455

<210> SEQ ID NO 7
<211> LENGTH: 455
<212> TYPE: PRT
<213> ORGANISM: Artificial Sequence
<220> FEATURE:
<223> OTHER INFORMATION: Caninised anti-NGF VH aglycosyl canine
      immunoglobulin heavy chain type C (caN-HCC*)

<400> SEQUENCE: 7

Glu Val Gln Leu Val Glu Ser Gly Gly Asp Leu Val Asn Pro Gly Gly
1               5                   10                  15

Thr Leu Thr Leu Ser Cys Val Val Ser Gly Phe Ser Leu Thr Asn Asn
            20                  25                  30

Asn Val Asn Trp Val Arg Gln Ala Leu Gly Arg Gly Leu Glu Trp Val
        35                  40                  45

Gly Gly Val Trp Ala Gly Gly Ala Thr Asp Tyr Asn Ser Ala Leu Lys
    50                  55                  60

Ser Arg Leu Thr Ile Thr Arg Asp Thr Ser Lys Ser Thr Val Phe Leu
65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Thr Leu Tyr Ala Met Asp Ala Trp
            100                 105                 110

Gly Gln Gly Thr Leu Val Thr Val Ser Ser Ala Ser Thr Thr Ala Pro
        115                 120                 125

Ser Val Phe Pro Leu Ala Pro Ser Cys Gly Ser Gln Ser Gly Ser Thr
    130                 135                 140

Val Ala Leu Ala Cys Leu Val Ser Gly Tyr Ile Pro Glu Pro Val Thr
145                 150                 155                 160

Val Ser Trp Asn Ser Val Ser Leu Thr Ser Gly Val His Thr Phe Pro
                165                 170                 175

Ser Val Leu Gln Ser Ser Gly Leu Tyr Ser Leu Ser Ser Met Val Thr
            180                 185                 190

Val Pro Ser Ser Arg Trp Pro Ser Glu Thr Phe Thr Cys Asn Val Ala
        195                 200                 205

His Pro Ala Thr Asn Thr Lys Val Asp Lys Pro Val Ala Lys Glu Cys
    210                 215                 220

Glu Cys Lys Cys Asn Cys Asn Asn Cys Pro Cys Pro Gly Cys Gly Leu
225                 230                 235                 240

Leu Gly Gly Pro Ser Val Phe Ile Phe Pro Pro Lys Pro Lys Asp Ile
                245                 250                 255
```

```
Leu Val Thr Ala Arg Thr Pro Thr Val Thr Cys Val Val Asp Leu
            260                 265                 270

Asp Pro Glu Asn Pro Glu Val Gln Ile Ser Trp Phe Val Asp Ser Lys
        275                 280                 285

Gln Val Gln Thr Ala Asn Thr Gln Pro Arg Glu Glu Gln Ser Ala Gly
    290                 295                 300

Thr Tyr Arg Val Val Ser Val Leu Pro Ile Gly His Gln Asp Trp Leu
305                 310                 315                 320

Ser Gly Lys Gln Phe Lys Cys Lys Val Asn Asn Lys Ala Leu Pro Ser
                325                 330                 335

Pro Ile Glu Glu Ile Ile Ser Lys Thr Pro Gly Gln Ala His Gln Pro
            340                 345                 350

Asn Val Tyr Val Leu Pro Pro Ser Arg Asp Glu Met Ser Lys Asn Thr
        355                 360                 365

Val Thr Leu Thr Cys Leu Val Lys Asp Phe Phe Pro Pro Glu Ile Asp
370                 375                 380

Val Glu Trp Gln Ser Asn Gly Gln Gln Glu Pro Glu Ser Lys Tyr Arg
385                 390                 395                 400

Met Thr Pro Pro Gln Leu Asp Glu Asp Gly Ser Tyr Phe Leu Tyr Ser
                405                 410                 415

Lys Leu Ser Val Asp Lys Ser Arg Trp Gln Arg Gly Asp Thr Phe Ile
            420                 425                 430

Cys Ala Val Met His Glu Ala Leu His Asn His Tyr Thr Gln Ile Ser
        435                 440                 445

Leu Ser His Ser Pro Gly Lys
    450                 455

<210> SEQ ID NO 8
<211> LENGTH: 331
<212> TYPE: PRT
<213> ORGANISM: Artificial Sequence
<220> FEATURE:
<223> OTHER INFORMATION: Canine immunoglobulin heavy chain type A Fc
      domain (HCA)

<400> SEQUENCE: 8

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu His Ser
    50                  55                  60

Leu Ser Ser Met Val Thr Val Pro Ser Ser Arg Trp Pro Ser Glu Thr
65                  70                  75                  80

Phe Thr Cys Asn Val Val His Pro Ala Ser Asn Thr Lys Val Asp Lys
                85                  90                  95

Pro Val Phe Asn Glu Cys Arg Cys Thr Asp Thr Pro Pro Cys Pro Val
            100                 105                 110

Pro Glu Pro Leu Gly Gly Pro Ser Val Leu Ile Phe Pro Pro Lys Pro
        115                 120                 125

Lys Asp Ile Leu Arg Ile Thr Arg Thr Pro Glu Val Thr Cys Val Val
    130                 135                 140

Leu Asp Leu Gly Arg Glu Asp Pro Glu Val Gln Ile Ser Trp Phe Val
145                 150                 155                 160
```

```
Asp Gly Lys Glu Val His Thr Ala Lys Thr Gln Ser Arg Glu Gln Gln
            165                 170                 175

Phe Asn Gly Thr Tyr Arg Val Val Ser Val Leu Pro Ile Glu His Gln
        180                 185                 190

Asp Trp Leu Thr Gly Lys Glu Phe Lys Cys Arg Val Asn His Ile Asp
    195                 200                 205

Leu Pro Ser Pro Ile Glu Arg Thr Ile Ser Lys Ala Arg Gly Arg Ala
210                 215                 220

His Lys Pro Ser Val Tyr Val Leu Pro Pro Ser Pro Lys Glu Leu Ser
225                 230                 235                 240

Ser Ser Asp Thr Val Ser Ile Thr Cys Leu Ile Lys Asp Phe Tyr Pro
                245                 250                 255

Pro Asp Ile Asp Val Glu Trp Gln Ser Asn Gly Gln Gln Glu Pro Glu
            260                 265                 270

Arg Lys His Arg Met Thr Pro Pro Gln Leu Asp Glu Asp Gly Ser Tyr
        275                 280                 285

Phe Leu Tyr Ser Lys Leu Ser Val Asp Lys Ser Arg Trp Gln Gln Gly
    290                 295                 300

Asp Pro Phe Thr Cys Ala Val Met His Glu Thr Leu Gln Asn His Tyr
305                 310                 315                 320

Thr Asp Leu Ser Leu Ser His Ser Pro Gly Lys
                325                 330

<210> SEQ ID NO 9
<211> LENGTH: 335
<212> TYPE: PRT
<213> ORGANISM: Artificial Sequence
<220> FEATURE:
<223> OTHER INFORMATION: Canine immunoglobulin heavy chain type B Fc
      domain (HCB)

<400> SEQUENCE: 9

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
```

```
            180                 185                 190
Pro Ile Gly His Gln Asp Trp Leu Lys Gly Lys Gln Phe Thr Cys Lys
                195                 200                 205
Val Asn Asn Lys Ala Leu Pro Ser Pro Ile Glu Arg Thr Ile Ser Lys
            210                 215                 220
Ala Arg Gly Gln Ala His Gln Pro Ser Val Tyr Val Leu Pro Pro Ser
225                 230                 235                 240
Arg Glu Glu Leu Ser Lys Asn Thr Val Ser Leu Thr Cys Leu Ile Lys
                245                 250                 255
Asp Phe Tyr Pro Pro Asp Ile Asp Val Glu Trp Gln Ser Asn Gly Gln
            260                 265                 270
Gln Glu Pro Glu Ser Lys Tyr Arg Thr Thr Pro Pro Gln Leu Asp Glu
        275                 280                 285
Asp Gly Ser Tyr Phe Leu Tyr Ser Lys Leu Ser Val Asp Lys Ser Arg
    290                 295                 300
Trp Gln Arg Gly Asp Thr Phe Ile Cys Ala Val Met His Glu Ala Leu
305                 310                 315                 320
His Asn His Tyr Thr Gln Glu Ser Leu Ser His Ser Pro Gly Lys
                325                 330                 335

<210> SEQ ID NO 10
<211> LENGTH: 333
<212> TYPE: PRT
<213> ORGANISM: Artificial Sequence
<220> FEATURE:
<223> OTHER INFORMATION: Canine immunoglobulin heavy chain type C Fc
      domain (HCC)

<400> SEQUENCE: 10

Ala Ser Thr Thr Ala Pro Ser Val Phe Pro Leu Ala Pro Ser Cys Gly
1               5                   10                  15
Ser Gln Ser Gly Ser Thr Val Ala Leu Ala Cys Leu Val Ser Gly Tyr
            20                  25                  30
Ile Pro Glu Pro Val Thr Val Ser Trp Asn Ser Val Ser Leu Thr Ser
        35                  40                  45
Gly Val His Thr Phe Pro Ser Val Leu Gln Ser Ser Gly Leu Tyr Ser
    50                  55                  60
Leu Ser Ser Met Val Thr Val Pro Ser Ser Arg Trp Pro Ser Glu Thr
65                  70                  75                  80
Phe Thr Cys Asn Val Ala His Pro Ala Thr Asn Thr Lys Val Asp Lys
                85                  90                  95
Pro Val Ala Lys Glu Cys Glu Cys Lys Cys Asn Cys Asn Asn Cys Pro
            100                 105                 110
Cys Pro Gly Cys Gly Leu Leu Gly Gly Pro Ser Val Phe Ile Phe Pro
        115                 120                 125
Pro Lys Pro Lys Asp Ile Leu Val Thr Ala Arg Thr Pro Thr Val Thr
    130                 135                 140
Cys Val Val Val Asp Leu Asp Pro Glu Asn Pro Glu Val Gln Ile Ser
145                 150                 155                 160
Trp Phe Val Asp Ser Lys Gln Val Gln Thr Ala Asn Thr Gln Pro Arg
                165                 170                 175
Glu Glu Gln Ser Asn Gly Thr Tyr Arg Val Val Ser Val Leu Pro Ile
            180                 185                 190
Gly His Gln Asp Trp Leu Ser Gly Lys Gln Phe Lys Cys Lys Val Asn
        195                 200                 205
```

```
Asn Lys Ala Leu Pro Ser Pro Ile Glu Glu Ile Ile Ser Lys Thr Pro
    210                 215                 220
Gly Gln Ala His Gln Pro Asn Val Tyr Val Leu Pro Pro Ser Arg Asp
225                 230                 235                 240
Glu Met Ser Lys Asn Thr Val Thr Leu Thr Cys Leu Val Lys Asp Phe
                245                 250                 255
Phe Pro Pro Glu Ile Asp Val Glu Trp Gln Ser Asn Gly Gln Gln Glu
            260                 265                 270
Pro Glu Ser Lys Tyr Arg Met Thr Pro Pro Gln Leu Asp Glu Asp Gly
        275                 280                 285
Ser Tyr Phe Leu Tyr Ser Lys Leu Ser Val Asp Lys Ser Arg Trp Gln
290                 295                 300
Arg Gly Asp Thr Phe Ile Cys Ala Val Met His Glu Ala Leu His Asn
305                 310                 315                 320
His Tyr Thr Gln Ile Ser Leu Ser His Ser Pro Gly Lys
                325                 330

<210> SEQ ID NO 11
<211> LENGTH: 331
<212> TYPE: PRT
<213> ORGANISM: Artificial Sequence
<220> FEATURE:
<223> OTHER INFORMATION: Canine immunoglobulin heavy chain type D Fc
      domain (HCD)

<400> SEQUENCE: 11

Ala Ser Thr Thr Ala Pro Ser Val Phe Pro Leu Ala Pro Ser Cys Gly
1               5                   10                  15
Ser Thr Ser Gly Ser Thr Val Ala Leu Ala Cys Leu Val Ser Gly Tyr
                20                  25                  30
Phe Pro Glu Pro Val Thr Val Ser Trp Asn Ser Gly Ser Leu Thr Ser
            35                  40                  45
Gly Val His Thr Phe Pro Ser Val Leu Gln Ser Ser Gly Leu Tyr Ser
        50                  55                  60
Leu Ser Ser Thr Val Thr Val Pro Ser Ser Arg Trp Pro Ser Glu Thr
65                  70                  75                  80
Phe Thr Cys Asn Val Val His Pro Ala Ser Asn Thr Lys Val Asp Lys
                85                  90                  95
Pro Val Pro Lys Glu Ser Thr Cys Lys Cys Ile Ser Pro Cys Pro Val
            100                 105                 110
Pro Glu Ser Leu Gly Gly Pro Ser Val Phe Ile Phe Pro Pro Lys Pro
        115                 120                 125
Lys Asp Ile Leu Arg Ile Thr Arg Thr Pro Glu Ile Thr Cys Val Val
130                 135                 140
Leu Asp Leu Gly Arg Glu Asp Pro Glu Val Gln Ile Ser Trp Phe Val
145                 150                 155                 160
Asp Gly Lys Glu Val His Thr Ala Lys Thr Gln Pro Arg Glu Gln Gln
                165                 170                 175
Phe Asn Ser Thr Tyr Arg Val Val Ser Val Leu Pro Ile Glu His Gln
            180                 185                 190
Asp Trp Leu Thr Gly Lys Glu Phe Lys Cys Arg Val Asn His Ile Gly
        195                 200                 205
Leu Pro Ser Pro Ile Glu Arg Thr Ile Ser Lys Ala Arg Gly Gln Ala
210                 215                 220
His Gln Pro Ser Val Tyr Val Leu Pro Pro Ser Pro Lys Glu Leu Ser
225                 230                 235                 240
```

```
Ser Ser Asp Thr Val Thr Leu Thr Cys Leu Ile Lys Asp Phe Tyr Pro
            245                 250                 255

Pro Glu Ile Asp Val Glu Trp Gln Ser Asn Gly Gln Pro Glu Pro Glu
        260                 265                 270

Ser Lys Tyr His Thr Thr Ala Pro Gln Leu Asp Glu Asp Gly Ser Tyr
    275                 280                 285

Phe Leu Tyr Ser Lys Leu Ser Val Asp Lys Ser Arg Trp Gln Gln Gly
290                 295                 300

Asp Thr Phe Thr Cys Ala Val Met His Glu Ala Leu Gln Asn His Tyr
305                 310                 315                 320

Thr Asp Leu Ser Leu Ser His Ser Pro Gly Lys
            325                 330
```

<210> SEQ ID NO 12
<211> LENGTH: 331
<212> TYPE: PRT
<213> ORGANISM: Artificial Sequence
<220> FEATURE:
<223> OTHER INFORMATION: Aglycosyl canine immunoglobulin heavy chain
      type A Fc domain (HCA*)

<400> SEQUENCE: 12

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu His Ser
    50                  55                  60

Leu Ser Ser Met Val Thr Val Pro Ser Ser Arg Trp Pro Ser Glu Thr
65                  70                  75                  80

Phe Thr Cys Asn Val Val His Pro Ala Ser Asn Thr Lys Val Asp Lys
                85                  90                  95

Pro Val Phe Asn Glu Cys Arg Cys Thr Asp Thr Pro Pro Cys Pro Val
            100                 105                 110

Pro Glu Pro Leu Gly Gly Pro Ser Val Leu Ile Phe Pro Pro Lys Pro
        115                 120                 125

Lys Asp Ile Leu Arg Ile Thr Arg Thr Pro Glu Val Thr Cys Val Val
    130                 135                 140

Leu Asp Leu Gly Arg Glu Asp Pro Glu Val Gln Ile Ser Trp Phe Val
145                 150                 155                 160

Asp Gly Lys Glu Val His Thr Ala Lys Thr Gln Ser Arg Glu Gln Gln
                165                 170                 175

Phe Ala Gly Thr Tyr Arg Val Val Ser Val Leu Pro Ile Glu His Gln
            180                 185                 190

Asp Trp Leu Thr Gly Lys Glu Phe Lys Cys Arg Val Asn His Ile Asp
        195                 200                 205

Leu Pro Ser Pro Ile Glu Arg Thr Ile Ser Lys Ala Arg Gly Arg Ala
    210                 215                 220

His Lys Pro Ser Val Tyr Val Leu Pro Pro Ser Pro Lys Glu Leu Ser
225                 230                 235                 240

Ser Ser Asp Thr Val Ser Ile Thr Cys Leu Ile Lys Asp Phe Tyr Pro
                245                 250                 255

Pro Asp Ile Asp Val Glu Trp Gln Ser Asn Gly Gln Gln Glu Pro Glu
            260                 265                 270
```

```
                    260                 265                 270
Arg Lys His Arg Met Thr Pro Pro Gln Leu Asp Glu Asp Gly Ser Tyr
            275                 280                 285

Phe Leu Tyr Ser Lys Leu Ser Val Asp Lys Ser Arg Trp Gln Gln Gly
            290                 295                 300

Asp Pro Phe Thr Cys Ala Val Met His Glu Thr Leu Gln Asn His Tyr
305                 310                 315                 320

Thr Asp Leu Ser Leu Ser His Ser Pro Gly Lys
            325                 330
```

<210> SEQ ID NO 13
<211> LENGTH: 335
<212> TYPE: PRT
<213> ORGANISM: Artificial Sequence
<220> FEATURE:
<223> OTHER INFORMATION: Aglycosyl caninised immunoglobulin heavy chain type B Fc domain (HCB*)

<400> SEQUENCE: 13

```
Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
            35                  40                  45

Gly Val His Thr Phe Pro Ser Val Leu Gln Ser Ser Gly Leu Tyr Ser
        50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
            115                 120                 125

Phe Pro Pro Lys Pro Lys Asp Thr Leu Leu Ile Ala Arg Thr Pro Glu
        130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Ala Gly Thr Tyr Arg Val Val Ser Val Leu
            180                 185                 190

Pro Ile Gly His Gln Asp Trp Leu Lys Gly Lys Gln Phe Thr Cys Lys
            195                 200                 205

Val Asn Asn Lys Ala Leu Pro Ser Pro Ile Glu Arg Thr Ile Ser Lys
        210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Tyr Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
            275                 280                 285
```

```
Asp Gly Ser Tyr Phe Leu Tyr Ser Lys Leu Ser Val Asp Lys Ser Arg
        290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335

<210> SEQ ID NO 14
<211> LENGTH: 333
<212> TYPE: PRT
<213> ORGANISM: Artificial Sequence
<220> FEATURE:
<223> OTHER INFORMATION: Aglycosyl canine immunoglobulin heavy chain
      type C Fc domain (HCC*)

<400> SEQUENCE: 14

Ala Ser Thr Thr Ala Pro Ser Val Phe Pro Leu Ala Pro Ser Cys Gly
1               5                   10                  15

Ser Gln Ser Gly Ser Thr Val Ala Leu Ala Cys Leu Val Ser Gly Tyr
            20                  25                  30

Ile Pro Glu Pro Val Thr Val Ser Trp Asn Ser Val Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Thr Asn Thr Lys Val Asp Lys
                85                  90                  95

Pro Val Ala Lys Glu Cys Glu Cys Lys Cys Asn Cys Asn Asn Cys Pro
            100                 105                 110

Cys Pro Gly Cys Gly Leu Leu Gly Gly Pro Ser Val Phe Ile Phe Pro
        115                 120                 125

Pro Lys Pro Lys Asp Ile Leu Val Thr Ala Arg Thr Pro Thr Val Thr
    130                 135                 140

Cys Val Val Val Asp Leu Asp Pro Glu Asn Pro Glu Val Gln Ile Ser
145                 150                 155                 160

Trp Phe Val Asp Ser Lys Gln Val Gln Thr Ala Asn Thr Gln Pro Arg
                165                 170                 175

Glu Glu Gln Ser Ala Gly Thr Tyr Arg Val Val Ser Val Leu Pro Ile
            180                 185                 190

Gly His Gln Asp Trp Leu Ser Gly Lys Gln Phe Lys Cys Lys Val Asn
        195                 200                 205

Asn Lys Ala Leu Pro Ser Pro Ile Glu Glu Ile Ile Ser Lys Thr Pro
    210                 215                 220

Gly Gln Ala His Gln Pro Asn Val Tyr Val Leu Pro Pro Ser Arg Asp
225                 230                 235                 240

Glu Met Ser Lys Asn Thr Val Thr Leu Thr Cys Leu Val Lys Asp Phe
                245                 250                 255

Phe Pro Pro Glu Ile Asp Val Glu Trp Gln Ser Asn Gly Gln Gln Glu
            260                 265                 270

Pro Glu Ser Lys Tyr Arg Met Thr Pro Pro Gln Leu Asp Glu Asp Gly
        275                 280                 285

Ser Tyr Phe Leu Tyr Ser Lys Leu Ser Val Asp Lys Ser Arg Trp Gln
    290                 295                 300

Arg Gly Asp Thr Phe Ile Cys Ala Val Met His Glu Ala Leu His Asn
305                 310                 315                 320
```

His Tyr Thr Gln Ile Ser Leu Ser His Ser Pro Gly Lys
            325                 330

<210> SEQ ID NO 15
<211> LENGTH: 331
<212> TYPE: PRT
<213> ORGANISM: Artificial Sequence
<220> FEATURE:
<223> OTHER INFORMATION: Canine immunoglobulin heavy chain type D Fc
      domain (HCD*)

<400> SEQUENCE: 15

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Thr Val Thr Val Pro Ser Ser Arg Trp Pro Ser Glu Thr
65                  70                  75                  80

Phe Thr Cys Asn Val Val His Pro Ala Ser Asn Thr Lys Val Asp Lys
                85                  90                  95

Pro Val Pro Lys Glu Ser Thr Cys Lys Cys Ile Ser Pro Cys Pro Val
            100                 105                 110

Pro Glu Ser Leu Gly Gly Pro Ser Val Phe Ile Phe Pro Pro Lys Pro
        115                 120                 125

Lys Asp Ile Leu Arg Ile Thr Arg Thr Pro Glu Ile Thr Cys Val Val
130                 135                 140

Leu Asp Leu Gly Arg Glu Asp Pro Glu Val Gln Ile Ser Trp Phe Val
145                 150                 155                 160

Asp Gly Lys Glu Val His Thr Ala Lys Thr Gln Pro Arg Glu Gln Gln
                165                 170                 175

Phe Ala Ser Thr Tyr Arg Val Val Ser Val Leu Pro Ile Glu His Gln
            180                 185                 190

Asp Trp Leu Thr Gly Lys Glu Phe Lys Cys Arg Val Asn His Ile Gly
        195                 200                 205

Leu Pro Ser Pro Ile Glu Arg Thr Ile Ser Lys Ala Arg Gly Gln Ala
    210                 215                 220

His Gln Pro Ser Val Tyr Val Leu Pro Pro Ser Pro Lys Glu Leu Ser
225                 230                 235                 240

Ser Ser Asp Thr Val Thr Leu Thr Cys Leu Ile Lys Asp Phe Tyr Pro
                245                 250                 255

Pro Glu Ile Asp Val Glu Trp Gln Ser Asn Gly Gln Pro Glu Pro Glu
            260                 265                 270

Ser Lys Tyr His Thr Thr Ala Pro Gln Leu Asp Glu Asp Gly Ser Tyr
        275                 280                 285

Phe Leu Tyr Ser Lys Leu Ser Val Asp Lys Ser Arg Trp Gln Gln Gly
    290                 295                 300

Asp Thr Phe Thr Cys Ala Val Met His Glu Ala Leu Gln Asn His Tyr
305                 310                 315                 320

Thr Asp Leu Ser Leu Ser His Ser Pro Gly Lys
                325                 330

THERAPEUTIC CANINE IMMUNOGLOBULINS AND METHODS OF USING SAME

FIELD OF THE INVENTION

The present invention relates to canine or canine derived antibodies, which have specific heavy chain constant regions, for use as antagonists of soluble extracellular mediators and/or cell surface receptors. The invention extends to the therapeutic use of the antibodies, or fragments thereof, in methods for the selective treatment of conditions such as inflammation, pain, cancer or infection in a canine subject.

BACKGROUND TO THE INVENTION

Recombinant immunoglobulins and fusion proteins constructed using constant domain fragments of immunoglobulins are used to treat many human diseases including inflammatory diseases (e.g. rheumatoid arthritis, psoriasis, inflammatory bowel disease), allergies (e.g. asthma), cancers (e.g. lymphoma, breast cancer, bowel cancer), infectious diseases (e.g. RSV infection), pain (e.g. osteoarthritic pain, cancer pain, lower back pain) and eye disease (e.g. age-related macular degeneration).

The molecular targets for therapy include cytokines and chemokines (e.g. interleukin-1 (IL-1), interleukin-5 (IL-5), granulocyte colony-stimulating factor (GCSF), granulocyte-macrophage colony stimulating factor), growth factors (e.g. nerve growth factor (NGF), vascular endothelial cell growth factor (VEGF), tumour necrosis factor (TNF)), cell surface receptors (e.g. HER-2, VEGFR, EGFR, CD20), cell surface-bound growth factors (e.g. unprocessed tumour necrosis factor), viruses (e.g. RSV) and components of the complement cascade (e.g. C5). Many other targets that have evidence for involvement in disease processes are known (e.g. as described in the IMGT/MAb-DB database Version 1.3.1 14 Dec. 2011, (www.imgt.org/mAb-DB/query).

Native immunoglobulins are produced as different major subtypes, including immunoglobulin G (IgG), immunoglobulin A (IgA), immunoglobulin M (IgM) or immunoglobulin E (IgE) and in response to infection these immunoglobulins play various roles in pathogen recognition by binding to target antigens, neutralisation, destruction and removal. Immunoglobulin G is produced as several different isotypes (also known as isoforms), such as (in humans) IgG1, IgG2, IgG3 and IgG4. These antibody isotypes vary in structure, in particular with regard to differences in the amino acid sequences of the constant region, particularly around the hinge region of the constant domain (Fc) between the C1 and C2 domains.

Different antibody isotypes also differ in terms of the downstream effector functions which the antibody mediates. For example, the constant region sequence of an antibody can mediate a strong influence on characteristics such as effector functions (ADCC, complement fixing and activation), pharmacokinetics, and physical properties of an antibody. Antibodies having different isotypes also differ in terms of their ability to bind to IgG Fc receptors on immune cells. In humans, IgG1 and IgG3 are active in recruiting complement to aid in target destruction by the cascade of complement enzymes in the blood (CDC: complement-dependent cytotoxicity), and similarly IgG1 and IgG3 bind Fc receptors on immune cells that target the bound antigen for destruction by antibody-mediated cellular cytotoxicity (ADCC). By contrast, IgG2 and IgG4 do not recruit complement or activate ADCC mediated attack and simply bind to the target antigen with high affinity to inhibit or neutralise its activity.

Recombinant immunoglobulins and fusion proteins made from the same are designed to take into account the activity of the Fc isotype when considering the target for disease intervention. For example, it is preferable when considering a therapeutic approach which aims to use antibodies for the targeted killing of human cancer cells to construct the recombinant immunoglobulin from IgG1 or IgG3 isotype Fc domains, as the use of these isotypes will drive immune mediated destructive mechanisms such as CDC and ADCC. By contrast, when targeting soluble mediators in the context of sensitive human tissues, the Fc domain is either omitted (e.g. in treatment of human age-related macular degeneration Fab fragments targeting VEGF are preferred), or is constructed using IgG2 or IgG4 Fc domains (e.g. targeting nerve growth factor in the context of neuropathic or inflammatory pain, or complement C5 in nephritis, psoriasis or rheumatoid arthritis). These considerations also apply to immunoglobulin fusion proteins, such as soluble TNF receptor Fc fusion proteins in the treatment of conditions such as rheumatoid arthritis, which are based on human IgG1 Fc therapeutics.

In canines and other species such as mice and horses, immunoglobulin isoforms also exist but have insufficient homology between one another to determine a priori which sequence will be active or inactive in inducing downstream effector functions such as CDC or ADCC. Furthermore, the number of immunoglobulins varies between species (e.g. in dog there are four IgG immunoglobulins, these being defined as calgG-A, calgG-B, calgG-C, and calgG-D (Tang et al., 2001). In horses, there are seven IgG isotypes (Wagner, 2006).

It is not possible to determine from sequence analysis or sequence homology alone whether a specific immunoglobulin isotype of a non-human species will be active or inactive in terms of mediating Fc receptor binding and downstream effector function. However, if these were known, it would be of significant value as the choice of isotype constant regions for antibody generation can be critical in order to provide the therapeutic effectiveness of an antibody or antibody based therapeutics, such as an antibody binding fragment or fusion protein.

SUMMARY OF THE INVENTION

Following extensive experimentation, it has been surprisingly identified by the present inventor that the isotypes of canine IgG immunoglobulin share the characteristics observed in human IgG antibodies that certain IgG antibody isotypes are active in terms of activating immune effector functions, while other IgG antibody isotypes do not activate immune effector functions and are accordingly inactive. Furthermore, of the four known canine heavy chain immunoglobulins (known as HCA (calgG-A), HCB (calgG-B), HCC (calgG-C) and HCD (calgG-D)), the inventor has surprisingly identified that heavy chain constant domains from two (calgG-B and calgG-C) of the four canine heavy chain immunoglobulins, when constructed as various recombinant forms targeting different therapeutic targets, surprisingly bind complement, whereas the other two (calgG-A and calgG-D) do not.

Accordingly, the present invention defines certain recombinant canine immunoglobulins, or fusion proteins made therefrom, which may be used in the therapy of canines where target destruction is desired (e.g. in cancer or infectious disease treatment); and certain other isoforms which may be preferred for therapeutic treatments in canines where target neutralisation alone, rather than target destruction, is desired (e.g. in the treatment of pain).

The present invention therefore provides recombinant canine immunoglobulins that can be distinguished by their ability or otherwise to bind to the first component of the complement cascade, based on the isotype of their heavy chain constant domain. As a result, and for the first time, recombinant canine immunoglobulins can be selected according to their intended use in treatment of disease in canines, whether for purposes where the intended target is selected for immune mediated destruction through complement mediated cytotoxicity (CDC; e.g. for use in killing canine tumours in vivo) or where the target is selected simply for neutralisation in the absence of undesirable immune mediated destruction (e.g. in the proximity of nerves, or in the eye).

According to a first aspect of the invention there is provided an antibody, fusion protein or a binding fragment thereof for use in the therapeutic treatment of a canine, wherein said antibody, fusion protein or binding fragment has a heavy chain constant domain comprising the amino acid sequence of SEQ ID NO:8, SEQ ID NO:11 or SEQ ID NO:13, wherein the amino acid sequence of the heavy chain minimises the activation of downstream immune system effector functions when the antibody, fusion protein or binding fragment is bound to its target antigen.

In certain embodiments, the therapeutic treatment of the canine relates to the treatment of pain or inflammation or a condition associated therewith, such as arthritis or an arthritic condition.

A yet further aspect of the invention provides use of an antibody, fusion protein or a binding fragment thereof comprising a heavy chain constant domain having the amino acid sequence of SEQ ID NO:8, SEQ ID NO:11 or SEQ ID NO:13, wherein the amino acid sequence of the heavy chain minimises the activation of downstream immune system effector functions when the antibody, fusion protein or binding fragment is bound to its target antigen, in the preparation of a medicament for use in the treatment of pain or inflammation in a canine subject or a condition associated therewith, such as arthritis or an arthritic condition.

A yet further aspect of the present invention provides a method for treating, inhibiting or ameliorating pain or inflammation or a condition associated therewith, such as arthritis or an arthritic condition, in a canine subject in need thereof, the method comprising the steps of:
provingd an antibody, fusion protein or a binding fragment thereof which binds specifically to a target antigen which has a specific function in the treatment or prevention of pain or inflammation, wherein the antibody, fusion protein or binding fragment thereof has a heavy chain constant domain comprising the amino acid sequence of SEQ ID NO:8, SEQ ID NO:11 or SEQ ID NO:13 and wherein the antibody, fusion protein or binding fragment thereof does not activate downstream immune system effector functions, and
administering a therapeutically effective amount of the antibody, fusion protein or binding fragment thereof to the canine subject.

A yet further aspect of the present invention provides a canine derived antibody, fusion protein or a binding fragment thereof which has a heavy chain constant domain comprising the amino acid sequence of SEQ ID NO:8, SEQ ID NO:11 or SEQ ID NO:13 for use in the preparation of a medicament for the treating, inhibiting or ameliorating pain or inflammation in a canine subject.

In certain embodiments, the pain is neuropathic pain. In particular, the pain may be peri-operative, post-operative or post-surgical pain. Post-operative pain may result following any operating procedure which in canines may include, but is not limited to orthopaedic surgery, soft tissue surgery, ovariohysterectomy procedures, castration procedures and the like. In certain further embodiments, the pain is chronic pain associated with cancer or a cancerous condition (oncologic pain). In certain further embodiments, the pain is associated with, or resulting from rheumatoid arthritis, osteoarthritis, inflammation or pruritis.

A yet further aspect of the present invention provides a method for the treatment of arthritis or an arthritic condition in a canine subject, the method comprising the steps of:
providing an antibody, fusion protein or a binding fragment thereof which binds specifically to a target antigen which has a specific function in the treatment or prevention of pain or inflammation, wherein the antibody, fusion protein or binding fragment thereof has a heavy chain constant domain comprising the amino acid sequence of SEQ ID NO:8, SEQ ID NO:11 or SEQ ID NO:13 and wherein the antibody, fusion protein or binding fragment thereof does not activate downstream immune system effector functions, and
administering a therapeutically effective amount of the antibody, fusion protein or binding fragment thereof to the canine subject in need of such treatment.

In certain embodiments, the foregoing method of the invention further comprises the step of co-administering at least one further agent which may enhance and/or complement the effectiveness of the antibody of the invention. For example, the antibody or antigen binding fragment thereof may be co-administered along with at least one analgesic, NSAID, opioid, corticosteroid or steroid. Examples of suitable analgesics include, but are not limited to butorphanol, 10 buprenorphine, fentanyl, flunixin meglumine, merpidine, morphine, nalbuphine and derivatives thereof. Suitable NSAIDS include, but are not limited to acetaminophen, acetylsalicylic acid, carprofen, etodolac, ketoprofen, meloxicam, firocoxib, robenacoxib, deracoxib and the like.

In certain embodiments, the foregoing methods may be accompanied by the administration of at least one further agent. Said agent may be a therapeutically active agent which may be one or more of the group selected from: an antibiotic, antifungal, antiprotozoal, antiviral or similar therapeutic agents. Furthermore the at least one further agent may be an inhibitor of mediator(s) of inflammation such as a PGE-receptor antagonist, an immunosuppressive agent, such as cyclosporine, an anti-inflammatory glucocorticoids. In certain further aspects the at least one further agent may be an agent which is used for the treatment of cognitive dysfunction or impairment, such as memory loss or related conditions which may become increasingly prevalent in older canines. Further still, the at least one further agent may be an anti-hypertensive or other compound used for the treatment of cardiovascular dysfunction, for example to treat hypertension, myocardial ischemia, congestive heart failure and the like. Further still, the at least one further agent may be a diuretic, vasodilator, beta-adrenergic receptor antagonist, angiotensin-II converting enzyme inhibitor, calcium channel blocker and HMG-CoA reductase inhibitor.

In certain embodiments of the foregoing aspects of the invention, the downstream immune system effector functions are selected from the group comprising complement dependent cytotoxicity (CDC), antibody dependent cell mediated cytotoxicity (ADCC), and antibody dependent cellular pathogenesis (ADCP). In specific embodiments, the amino acid sequence of the heavy chain constant domain inhibits binding of the heavy chain to C1q, this preventing induction of the complement cascade and complement dependent cytotoxicity (CDC).

In certain embodiments, the target antigen is a soluble mediator. In certain embodiments, the target antigen is nerve growth factor (NGF). In certain embodiments, the antibody specifically binds to and antagonises a receptor which mediates pain or inflammation. In certain further embodiments, the target antigen can be selected from the group consisting of, but not limited to: cytokines or chemokines (e.g. interleukin-1 and related interleukins IL-2 through IL-35, granulocyte colony-stimulating factor, granulocyte-macrophage colony stimulating factor, erythropoietin, thrombopoetin, leukaemia inhibitory factor, ciliary neurotrophic factor, oncostatin M), growth factors (e.g. nerve growth factor (NGF), brain-derived neurotrophic factor (BDNF), neurotrophin-3, neurotrophin-4, vascular endothelial cell growth factor (VEGF), tumour necrosis factor (TNF), cell surface receptors (e.g. HER-2, VEGFR, EGFR, CD20), cell surface-bound growth factors (e.g. unprocessed tumour necrosis factor), viruses (e.g. RSV) and components of the complement cascade (e.g. C5, C5a).

According to yet further aspect of the invention there is provided an antibody, fusion protein or a binding fragment thereof for use in the therapeutic treatment of a canine, wherein said antibody, fusion protein or binding fragment has a heavy chain constant domain comprising the amino acid sequence of SEQ ID NO:9, SEQ ID NO:10, or SEQ ID NO:14 wherein the amino acid sequence of the heavy chain mediates the activation of downstream immune system effector functions when the antibody, fusion protein or binding fragment is bound to its target antigen.

In certain embodiments, the therapeutic treatment of the canine relates to the treatment of a cancerous or malignant condition.

A yet further aspect of the invention provides use of an antibody, fusion protein or a binding fragment thereof comprising a heavy chain constant domain having the amino acid sequence of SEQ ID NO:9, SEQ ID NO:10 or SEQ ID NO:14, wherein the amino acid sequence of the heavy chain mediates the activation of downstream immune system effector functions when the antibody, fusion protein or binding fragment is bound to its target antigen, in the preparation of a medicament for use in the treatment of a cancerous or malignant condition in a canine subject.

A yet further aspect of the present invention provides a method for the treatment or prevention of a cancerous or malignant condition in a canine subject, the method comprising the steps of:
  providing an antibody, fusion protein or a binding fragment thereof which binds specifically to a target antigen which has a specific function in the treatment of a cancerous or malignant condition, wherein the antibody, fusion protein or binding fragment has a heavy chain constant domain comprising the amino acid sequence of SEQ ID NO:9, SEQ ID NO:10 or SEQ ID NO:14 and wherein the antibody, fusion protein or binding fragment activates downstream immune system effector functions, and
  administering a therapeutically effective amount of the antibody, fusion protein or binding fragment to the canine subject in need of such treatment.

In certain embodiments, the foregoing method of the invention further comprises the step of co-administering at least one further agent which may enhance and/or complement the effectiveness of the antibody of the invention.

A yet further aspect of the present invention provides use of a canine derived antibody, fusion protein or a binding fragment thereof, which has a heavy chain constant domain comprising the amino acid sequence of SEQ ID NO:9, SEQ ID NO:10 or SEQ ID NO:14 in the preparation of a medicament for the treatment of cancerous or malignant condition in a canine subject.

In certain embodiments of the foregoing aspects of the invention, the downstream immune system effector functions are selected from the group comprising complement dependent cytotoxicity (CDC), antibody dependent cell mediated cytotoxicity (ADCC), and antibody dependent cellular pathogenesis (ADCP). In specific embodiments, the amino acid sequence of the heavy chain constant domain provides for binding of the heavy chain to C1q, this inducing the complement cascade and complement dependent cytotoxicity (CDC). In certain embodiments, the heavy chain constant domain provides for binding to Fc receptors, which may in turn mediate ADCP and/or ADCC immune responses.

In certain embodiments, the target antigen is a cancer specific antigen. In certain further embodiments of the invention, the target antigen may be selected from the group of membrane bound proteins expressed on canine tumour cells. In further embodiments of the invention, the membrane bound canine tumour proteins may be selected from the group of proteins including CD2, CD4, CD8, CD20, EGFR, VEGFR, HER2 and the like. In certain further embodiments, the target antigen can be selected from the group consisting of, but not limited to: cytokines and chemokines (e.g. interleukin-1 (IL-1), IL-2, IL-3 and interleukins numerically through to IL-35, granulocyte colony-stimulating factor, granulocyte-macrophage colony stimulating factor, erythropoietin, thrombopoetin, leukaemia inhibitory factor, ciliary neurotrophic factor, oncostatin M), growth factors (e.g. nerve growth factor (NGF), brain-derived neurotrophic factor (BDNF), neurotrophin-3, neurotrophin-4, vascular endothelial cell growth factor (VEGF), tumour necrosis factor (TNF)), cell surface receptors (e.g. HER-2, VEGFR, EGFR, CD20), cell surface-bound growth factors (e.g. unprocessed tumour necrosis factor), viruses (e.g. RSV) and components of the complement cascade (e.g. C5, C5a).

A yet further aspect of the invention provides for an antibody, fusion protein or a binding fragment thereof for use in the treatment of a condition in a canine, wherein the antibody, fusion protein or binding fragment has a heavy chain constant domain which does not bind to C1q when the antibody, fusion protein or binding fragment is bound to its target antigen and wherein the antibody, fusion protein or binding fragment can be purified using Protein A chromatography.

In certain embodiments, said antibody, fusion protein or binding fragment has a heavy chain constant domain comprising the amino acid sequence of SEQ ID NO:13. In certain embodiments, said antibody, fusion protein or binding fragment has a heavy chain constant domain selected from the group consisting of SEQ ID NO:6, SEQ ID NO:12 and SEQ ID NO:15.

A yet further aspect of the invention provides use of an antibody, fusion protein or a binding fragment which comprises a heavy chain constant domain which does not bind to C1q when the antibody, fusion protein or binding fragment is bound to its target antigen and wherein the antibody, fusion protein or binding fragment can be purified using Protein A chromatography in the preparation of a medicament for the treatment of a condition associated with pain and/or inflammation in a canine.

In certain embodiments, said antibody, fusion protein or binding fragment has a heavy chain constant domain comprising the amino acid sequence of SEQ ID NO:13. In certain embodiments, said antibody, fusion protein or binding fragment has a heavy chain constant domain selected from the group consisting of SEQ ID NO:6, SEQ ID NO:12 and SEQ ID NO:15.

A yet further aspect of the present invention provides a method for treating, inhibiting or ameliorating pain or inflammation or a condition associated therewith, such as arthritis or an arthritic condition, in a canine subject in need thereof, the method comprising the steps of:
   providing an antibody, fusion protein or binding fragment which comprises a heavy chain constant domain which does not bind to C1q when the antibody is bound to its target antigen and wherein the antibody can be purified using Protein A chromatography, and
   administering a therapeutically effective amount of the antibody, fusion protein or binding fragment thereof to the canine subject.

In certain embodiments, said antibody, fusion protein or binding fragment has a heavy chain constant domain comprising the amino acid sequence of SEQ ID NO:13. In certain embodiments, said antibody, fusion protein or binding fragment has a heavy chain constant domain selected from the group consisting of SEQ ID NO:6, SEQ ID NO:12 and SEQ ID NO:15.

In various further aspects, the invention extends to: (i) nucleic acids which encode any of the foregoing antibodies, fusion proteins or antibody fragments of the invention, (ii) vectors which carry said nucleic acids, (iii) host cells carrying said vectors. The invention further extends to methods for producing antibodies and fusion proteins as defined in the foregoing statements of invention. In a yet further aspect, the present invention extends to pharmaceutical compositions which comprise the antibodies or fusion proteins of the present invention along with at least one carrier, diluent or excipient.

A further aspect of the invention provides a recombinant antibody, fusion protein or binding fragment thereof which can be therapeutically administered to a canine in order to specifically bind to a target antigen and which further mediates an immune response which is characterised by C1q complement binding to said antibody, fusion protein or binding fragment thereof and associated complement dependent cytotoxicity, wherein the heavy chain of the antibody, fusion protein or binding fragment thereof comprises canine immunoglobulin heavy chain constant domain isotype B (HCB, calgG-B) having an amino acid sequence of SEQ ID NO:9, canine immunoglobulin heavy chain constant domain isotype C (HCC, calgG-C) having an amino acid sequence of SEQ ID NO:10 or aglycosyl canine immunoglobulin heavy chain isotype C (HCC, calgG-C) having an amino acid sequence of SEQ ID NO:14.

A yet further aspect of the present invention provides use of an antibody, fusion protein or binding fragment thereof which comprises canine immunoglobulin heavy chain constant domain isotype B (HCB, calgG-B) having an amino acid sequence of SEQ ID NO:9, canine immunoglobulin heavy chain constant domain isotype C (HCC, calgG-C) having an amino acid sequence of SEQ ID NO:10 or aglycosyl canine immunoglobulin heavy chain isotype C (HCC, calgG-C) having an amino acid sequence of SEQ ID NO:14 in the preparation of a medicament for use in the treatment of a condition where specific binding to a target antigen is required and where an immune response which is characterised by C1q complement binding to said antibody, fusion protein or binding fragment thereof and associated complement dependent cytotoxicity is desirable.

A yet further aspect of the present invention provides a method for the treatment of a cancerous condition in a canine subject, the method comprising the step of:
   providing an immunoglobulin, fusion protein or a binding fragment thereof which has binding specificity for a tumour specific antigen and which further comprises canine immunoglobulin heavy chain constant domain isotype B (HCB, calgG-B) having an amino acid sequence of SEQ ID NO:9, canine immunoglobulin heavy chain constant domain isotype C (HCC, calgG-C) having an amino acid sequence of SEQ ID NO:10 or aglycosyl canine immunoglobulin heavy chain isotype C (HCC, calgG-C) having an amino acid sequence of SEQ ID NO:14, and
   administering a therapeutically effective amount of the immunoglobulin, fusion protein or binding fragment to the canine subject in need thereof.

In various further aspects, the invention extends to antibodies or fusion proteins which bind to a desired target antigen and which comprise heavy chain constant domains which do not bind C1q and which accordingly do not mediate an immune response involving complement dependent cytotoxicity.

Accordingly, in a yet further aspect of the present invention, there is provided a recombinant antibody, fusion protein or binding fragment thereof which can be therapeutically administered to a canine in order to specifically bind to a target antigen, wherein the constant domain of the antibody or fusion protein does not bind to C1q complement and wherein the heavy chain of the constant domain comprises canine immunoglobulin heavy chain constant domain isotype A (HCA, calgG-A) having an amino acid sequence of SEQ ID NO:8, canine immunoglobulin heavy chain constant domain isotype D (HCD, calgG-D) having an amino acid sequence of SEQ ID NO:11 or an aglycosyl canine immunoglobulin heavy chain constant domain isotype B having an amino acid sequence of SEQ ID NO:13 (HCB*, calgG-B).

A yet further aspect of the present invention provides use of an antibody, fusion protein or binding fragment thereof which comprises canine immunoglobulin heavy chain constant domain isotype A (HCA, calgG-A) having an amino acid sequence of SEQ ID NO:8, canine immunoglobulin heavy chain constant domain isotype D (HCD, calgG-D) having an amino acid sequence of SEQ ID NO:11 or an aglycosyl canine immunoglobulin heavy chain constant domain isotype B having an amino acid sequence of SEQ ID NO:13 (HCB*, calgG-B) in the preparation of a medicament for use in the treatment of a condition where specific binding to a target antigen is required and where an immune response which is characterised by C1q complement binding to said antibody, fusion protein or binding fragment thereof and associated complement dependent cytotoxicity is not desirable.

A yet further aspect of the present invention provides a method for the treatment of a condition in a canine subject, the method comprising the step of:
   providing an immunoglobulin, fusion protein or a binding fragment thereof which has binding specificity for a tumour specific antigen and which further comprises canine immunoglobulin heavy chain constant domain isotype A (HCA, calgG-A) having an amino acid sequence of SEQ ID NO:8, canine immunoglobulin heavy chain constant domain isotype D (HCD, calgG-D) having an amino acid sequence of SEQ ID NO:11 or an aglycosyl canine immunoglobulin heavy chain constant domain isotype B having an amino acid sequence of SEQ ID NO:13 (HCB*, calgG-B), and administering a therapeutically effective amount of the immunoglobulin, fusion protein or binding fragment to the canine subject in need thereof.

In certain embodiments, the aglycosylated constant domain designed for antibody construction in the absence of CDC activity is alanine-substituted aglycosylated heavy chain HCB having an amino acid sequence of SEQ ID NO:6 (denoted HCB*). In various further aspects of the invention, the antibodies incorporating heavy chains HCA, HCD or CDC inactive aglycosylated forms of HCA, HCB or HCD (HCA*, HCB* or HCD*: SEQ ID NO:12, SEQ ID NO:13 and SEQ ID NO:15) are directed to canine growth factors, hormones, cytokines, chemokines or other soluble mediators such as components of the complement cascade. In certain embodiments, the antibodies incorporating heavy chains HCA, HCD or HCB* are directed to canine nerve growth factor (NGF) for the purposes of neutralising canine NGF biological activity in a canine, without inducing CDC.

In certain embodiments of the foregoing aspects of the invention the antibody is a monoclonal antibody. In certain further embodiments, the antibody is a chimeric antibody. In some embodiments, the antibody is a caninised antibody, that is, an antibody which has an amino acid sequence which has been de-immunised such that neutralising antibodies will not be produced there against when administered to a canine subject. Typically the heavy chain constant domains of the antibody are selected or modified by way of amino acid substitution or deletion such that the constant domains do not mediate downstream effector functions. In certain embodiments, the antibody may be conjugated to at least one reporter molecule.

In certain further embodiments at least one residue in the constant domain of the antibodies or fusion proteins of the foregoing aspects of the invention can be substituted or deleted in order to prevent the glycosylation of that residue. In a further aspect of the invention the canine immunoglobulin heavy chain constant domain may be fused whole or in part to the extracellular domain of a cytokine or chemokine receptor or other trans-membrane protein (e.g. the TNF receptor), whereby the whole or fragment of the canine immunoglobulin heavy chain constant domain is selected from the group HCA, HCD or HCB* where it is desired that the canine extracellular domain-immunoglobulin heavy chain fusion protein does not activate CDC (e.g. where TNF receptor Fc fusion proteins are designed for the neutralization of soluble TNF) or conversely, the canine immunoglobulin heavy chain constant domain is selected from the group HCB, HCC or HCC* where it is desired that the canine extracellular domain-immunoglobulin heavy chain fusion protein (e.g. where TNF receptor Fc fusion proteins are designed to kill membrane-associated TNF bearing inflammatory cells).

In further aspects of the invention, the canine receptor-Fc fusion proteins may be selected from the group of extracellular domains of membrane bound receptors found on canine cells fused to canine immunoglobulin domain heavy chain Fc regions. In a further aspect of the invention, the antibodies incorporating heavy chains HCB, HCC or HCC* are directed to CD20 for the purposes of inducing CDC of canine CD20 expressing cells, such as canine lymphoma cells through the binding of these antibodies to CD20 on their surface.

Furthermore, it is preferred that the caninised antibodies are not cross-reactive to any other epitopes present in canines, and further that neutralising antibodies are not generated against the antibodies of the invention when they are administered to a canine.

In certain further embodiments, modifications to the amino acid sequence of the constant regions of the heavy chain may be made to the antibodies or fusion proteins of the invention. Said modification may involve the addition, substitution or deletion of one or more amino acid residues. Said amino acid changes are typically performed in order to modify the functional characteristics of the antibody. For example, amino acid modification may be performed to prevent downstream effector functions mediated by the antibody constant domains, for example by preventing the ability of the antibody to bind to Fc receptors, activate complement or induce ADCC. Furthermore, modifications may be made to the amino acid residues of the hinge region of the heavy chain constant domain in order to modify the circulatory half-life of an antibody when it is administered to a canine.

In some embodiments, the invention provides multi-specific or multivalent antibodies comprising an antibody or binding fragment of the invention coupled or conjoined to other antibodies with different binding specificities for use in combination therapy. A multi-specific antibody comprises at least one antibody or binding fragment specific to a first epitope, and at least one binding site specific to another epitope present on the antigen, or to a different antigen. A multivalent antibody comprises antibodies or antibody binding fragments which have binding specificity to the same epitope. Accordingly, in certain embodiments, the invention extends to an antibody fusion protein comprising four or more Fv regions or Fab regions of the antibodies of the present invention. In certain further embodiments, the invention extends to a bispecific antibody, wherein an antibody or binding fragment thereof according to the present invention is linked to a second antibody or binding fragment thereof which has binding specific for a second target, said target not being the first antigen. Such multivalent, bispecific or multispecific antibodies can be made by a variety of recombinant methods which would be well known to the person skilled in the art.

In certain embodiments, the antibody, fusion protein or antigen binding fragment is administered to the canine as part of the foregoing methods at a dose ranging from about 0.01 mg/kg of body weight to about 10 mg/kg of body weight, in particular from 0.03 mg/kg of body weight to about 3 mg/kg of body weight.

In various further aspects, the present invention extends to a composition comprising an antibody, fusion protein or binding fragment thereof according to any foregoing aspect of the invention. In certain embodiments, the composition further comprises at least one pharmaceutically acceptable carrier. In certain embodiments, the composition may further comprise at least one analgesic, NSAID, opioid, corticosteroid or steroid.

In various further aspects, the present invention extends to isolated nucleic acid which encodes the antibody, fusion protein or antibody binding fragments of the invention. Accordingly, a yet further aspect of the invention provides an isolated nucleic acid that encodes an antibody, fusion protein or antigen-binding fragment according to any of the foregoing aspects of the invention. In certain embodiments, the isolated nucleic acid further encodes one or more regulatory sequences operably linked thereto.

In a further aspect there is provided an expression vector comprising a polynucleotide encoding a heavy and/or light chain variable domain or a heavy and/or light chain constant domain of the invention. In certain embodiments the expression vector further comprises one or more regulatory sequences. In certain embodiments the vector is a plasmid or a retroviral vector. A yet further aspect provides a host cell incorporating the expression vector of the foregoing aspect of the invention. A further aspect of the invention provides a host cell which produces the antibody of any of the foregoing aspects of the invention.

A yet further aspect of the invention provides a method for producing an antibody or fusion protein of the invention, the method comprising the step of culturing the host cell of the foregoing aspect of the invention to allow the cell to express the antibody. A yet further aspect of the present invention provides a method of producing the antibody or fusion protein of the invention comprising the steps of expressing one or more of the polynucleotides/nucleic acids or vectors of the foregoing aspects of the invention which express the light and/or heavy chains of the antibodies of the invention in a suitable host cell, recovering the expressed polypeptides, which may be expressed together in a host cell, or separately in different host cells, and isolating antibodies. A yet further aspect of the invention provides a method for treating, ameliorating or inhibiting pain in a canine, the method comprising the step of administering to the canine an effective amount of a polynucleotide which encodes an antibody or fusion protein having a heavy chain constant domain comprising the amino acid sequence of SEQ ID NO:8-SEQ ID NO:11.

Canine Antibody Purification

In the case of those canine antibodies where target neutralisation is desired in the absence of unwanted immune effector activity, the present inventor has surprisingly discovered that native isoforms of canine heavy chains that lack CDC activity also bind *Staphylococcus* Protein A very poorly, if at all, and consequently this common method for purification of antibodies cannot be used in manufacture. The inventor describes three ways of overcoming this restriction, through the use of alternative purification strategies and through mutation of the heavy chain to prevent glycosylation during production. Purified antibodies prepared by these methods were produced by the inventor and shown to have the desirable properties of being safe and effective in-vivo in dogs without unwanted immunogenicity.

A yet further aspect of the invention provides a method for the purification of a canine derived immunoglobulin or an immunoglobulin or fusion protein comprising a canine heavy chain constant domain of isotype A (HCA, calgG-A) having an amino acid sequence of SEQ ID NO:8 or a canine immunoglobulin heavy chain constant domain of isotype D (HCD, calgG-D) having an amino acid sequence of SEQ ID NO:11 from a source mixture, the method comprising the steps of:
  (i) providing a source mixture comprising target immunoglobulins or fusion proteins,
  (ii) subjecting the source mixture to anion exchange chromatography;
  (iii) subjecting the source mixture to hydrophobic interaction chromatography; and
  (iv) subjecting the source mixture to size exclusion chromatography.

In certain embodiments, the method comprises the step of buffer exchange in phosphate buffered saline. Typically the method produces a purified antibody which is fractionated to high purity and bioactivity.

A further aspect of the present invention provides for the method of production of an aglycosylated canine antibody that can be purified by Protein A chromatography.

In various further aspects of the invention, there is provided a canine or canine derived antibody or fusion protein produced in accordance with any of the methods defined herein, for use in the therapeutic treatment of a canine. In various further aspects, there is provided the use of an anti-canine NGF antibody in the preparation of a medicament for use in treating an immune mediated condition, or a condition associated with pain, in a canine.

A yet further aspect of the invention provides a method for the purification of a canine derived immunoglobulin or an immunoglobulin or fusion protein comprising a canine heavy chain constant domain of isotype A (HCA, calgG-A) having an amino acid sequence of SEQ ID NO:8 or a canine immunoglobulin heavy chain constant domain of isotype D (HCD, calgG-D) having an amino acid sequence of SEQ ID NO:11 from a source mixture, the method comprising the steps of:
  (i) providing a source mixture comprising target immunoglobulins,
  (ii) subjecting the source mixture to captoadhere affinity chromatography; and
  (iii) subjecting the source mixture to anion exchange chromatography.

A yet further aspect of the present invention extends to an antibody or fusion protein produced from the purification method of the foregoing aspect of the invention for use in the treatment of a canine.

BRIEF DESCRIPTION OF THE FIGURES

FIGS. 4A, 4B and 4C show binding of complement to antibodies constructed using various canine heavy chain isotypes. Caninised monoclonal antibodies (MAb) were expressed in CHO cells and tested for their ability to bind complement C1q. Panel A—caninised anti-NGF antibodies (caN-HCB, caN-HCC) compared with humanised antibody isotypes (huN-G1, huN-G4); Panel B—anti-VEGF antibodies constructed with canine HCA (caV-HCA) and HCB (caV-HCB) isotypes; Panel C—anti-CD20 antibody constructed using HCB isotype (mub-HCA) compared with mouse IgG2a isotype (muB-2a).

FIG. 6A shows the results of fractionation by size exclusion HPLC. FIG. 6B shows a reducing SDS-PAGE gel of fractions following each step. FIG. 6C shows SDS-PAGE analysis under non-reducing and reducing conditions. In FIG. 6c, lane 1 is MWS, lane 2 is anti-canine NGF antibody 2 µg/mL and 0 µl reducing agent, lane 3 is anti-canine NGF antibody 4 µg/mL and 0 µl reducing agent, lane 4 is anti-canine NGF antibody 6 µg/mL and 0 µl reducing agent, lane 5 is MWS, lane 6 is anti-canine NGF antibody 2 µg/mL and 3 µl reducing agent, lane 7 is anti-canine NGF antibody 4 µg/mL and 3 µl reducing agent, lane 8 is anti-canine NGF antibody 6 µg/mL and 3 µl reducing agent and lane 9 is MWS.

FIG. 7 shows a comparison of anti-canine NGF antibody (HCA isotype) purified by Methods I and II. FIG. 7A: comparison by non-reducing and reducing SDS-PAGE.

FIG. 8 shows body weight (upper panel) and temperature (lower panel) are stable following intravenous administration of anti-canine NGF antibodies (HCA isotype, purified by Method I) into dogs.

DETAILED DESCRIPTION OF THE INVENTION

Following extensive experimentation, the inventor has designed and constructed several canine monoclonal antibodies using different heavy chain constant domain isotypes and has surprisingly shown that useful properties can be deduced from their ability (or otherwise) to mediate downstream effector functions and in particular from their ability to bind to complement. Accordingly, the inventor has identified different biological effects mediated by different canine immunoglobulin subtypes. For the complement-binding canine antibody isotypes, this useful property is in directing cells bound by the same antibodies for complement directed cytotoxicity (CDC) in-vivo. An example where this functional property is desirable is in canine cancer therapy where antibodies directed to tumour antigens would then direct the complement system to target the cells which have been bound by the antibody, for destruction.

By contrast, antibody isotypes which do not bind complement and so do not cause CDC are preferred where complement activity is undesirable, for example in the proximity of nerves, in the eye or in already inflamed tissues, or simply due to the desire to reduce the risk of an unforeseen side effect of antibody.

Clearly therefore, the ability to predict which canine isotypes are suitable for design and use of antibody therapies in canines is a highly desirable and useful.

Four different canine immunoglobulin G isotypes have been described (calgG-A (canine immunoglobulin G isotype A), calgG-B, calgG-C, and calgG-D—Tang et al., 2001). For simplicity (and to allow distinction of different antibody constructions and from light chain components) the heavy chain constant domains are termed HCA (calgG-A), HCB (calgG-B), HCC (calgG-C) and HCD calgG-D) herein.

Purification of Antibodies

Figure 5:
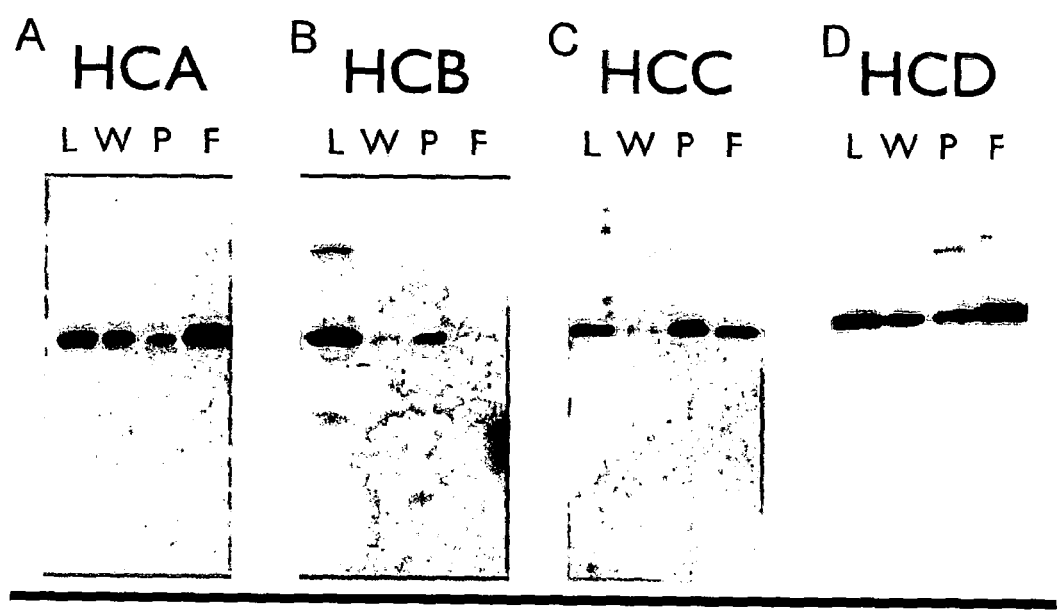
FIG. 5 shows relative recovery of anti-NGF antibody isotypes purified by Protein A and detected using anti-canine polyclonal immunoglobulin by Western blot. The supernatants from FIG. 1 were passed over Protein A columns and specifically bound material eluted. Equal volumes of eluate were subjected to SDS-PAGE. Canine isotypes HCA, HCC and HCD bound weakly to Protein A as indicated by significant material in the wash and flow through fractions. FIGS. A-D show relative recovery of canine antibody isotypes HCA, HCB, HCC and HCD by Protein A: L, load; W, wash; P, purified; F, flow through. Anti-NGF antibody supernatants from FIG. 1 were used in this experiment.

A further surprising discovery was made by the inventor in the process of purifying the desirable HCA and HCD isoforms of anti-NGF antibodies in that neither bound to Protein A, the ligand used at manufacture-scale in industry in the form of Protein A affinity column chromatography to produce large scale purification of therapeutic proteins. FIG. 5 shows the relative recovery of HCA, HCB, HCC and HCD isoforms of the anti-NGF antibodies by Protein A affinity chromatography at small scale. Consequently, other methods were needed to purify the HCA or HCD isoforms, as these could not be purified using Protein A affinity chromatography. After extensive experimentation, the inventor has surprisingly identified two alternative methods (referred to herein as Method I and Method II) which could be used to purify a caN-HCA-kLC antibody construct, or other canine antibodies which have the HCA or HCD heavy chain isotype.

The first method comprises a combination of anion exchange chromatography, hydrophobic interaction chromatography and size exclusion chromatography. The second method comprises a combination of captoadhere affinity chromatography and anion exchange chromatography. FIG. 6 illustrates the purification of the HCA containing anti-NGF antibody by each of the two methods. Highly purified material was obtained by each method and the two methods produced material with similar bioactivity by NGF ELISA (FIG. 7). Since the HCA and HCD isotypes are more similarly related to one another than to HCB and HCC isotypes, the methods are used for both isotypes.

In a further exploration of antibody purification, the inventor surprisingly found that the aglycosyl HCB* isotype anti-NGF antibody, like the HCB isotype was still able to bind Protein A and so has the desirable property of lack of CDC activity and purification by Protein A chromatography.

Canine Safety Testing

In order to demonstrate that the antibodies of the present invention, that are designed to have no unwanted CDC activity, are safe to give to dogs, the highly purified anti-NGF HCA isotype antibody was injected into three dogs by intravenous injection (following prior approval by the Institutional Animal Ethics Committee—CRL, Ireland). FIG. 8 shows that in addition to a lack of behavioural changes observed by the veterinarians, the three dogs showed no weight change or pyrexia following injection of HCA isotype antibody (single 2 mg/kg dose).

Figure 9:
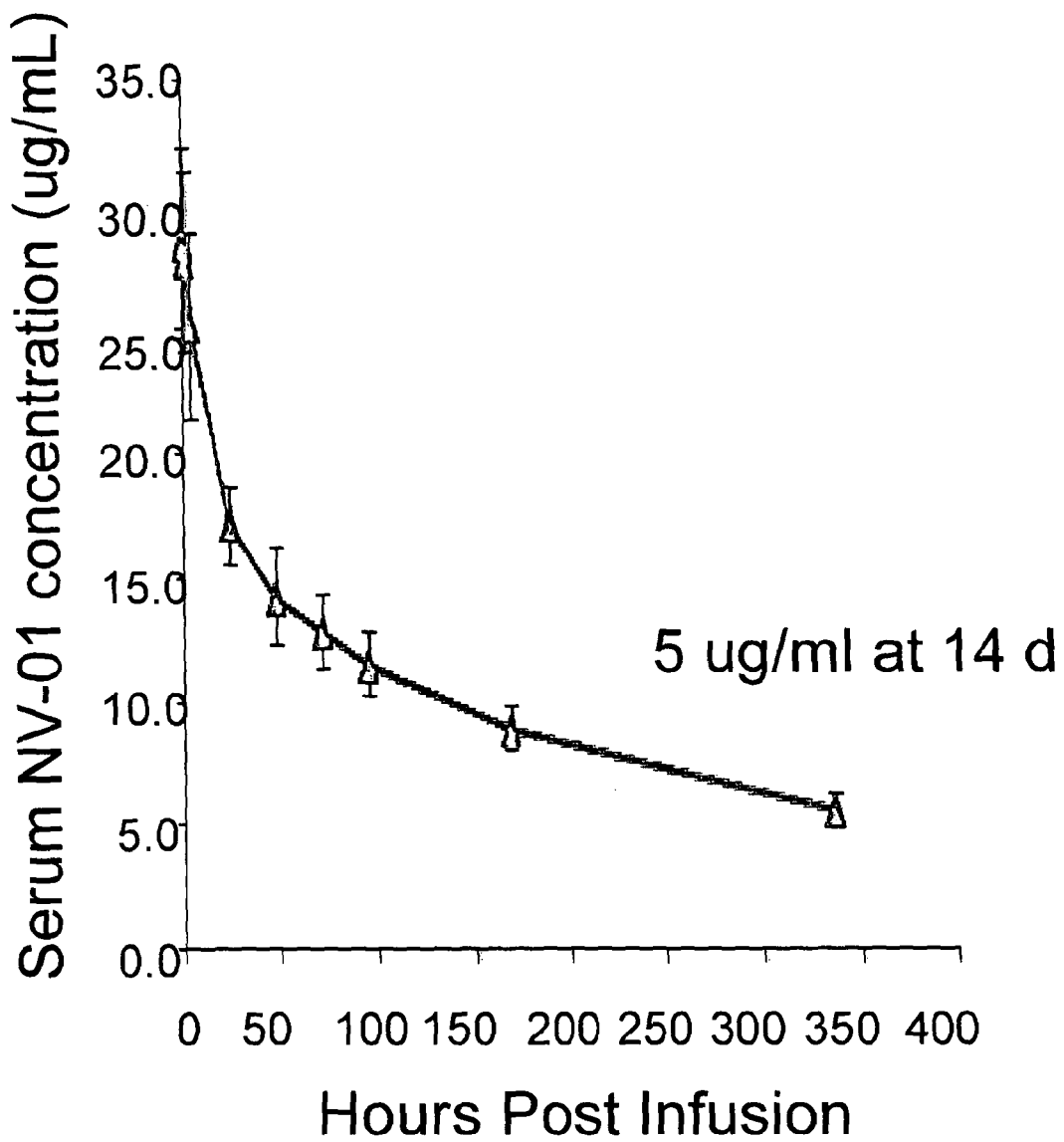
FIG. 9 shows kinetic analysis of plasma anti-canine NGF monoclonal antibody concentration following intravenous injection to a dog. A beagle dog was injected intravenously with anti-NGF antibody at 2 mg/kg, samples of plasma were taken at the times indicated and anti-NGF monoclonal antibody was detected by NGF ELISA. The anti-canine NGF monoclonal antibody had a surprisingly long elimination (beta) phase half life of approximately 9 days.

Plasma kinetics of the HCA isotype antibody in the three dogs was consistent with a two-phase distribution and clearance mechanism, including a long beta half-life of approximately 9 days (FIG. 9). The lack of rapid clearance over the 14 days follow up period was consistent with their being no anti-antibody response to the canine antibody. By contrast human immunoglobulin heavy chain constant domains are immunogenic in dogs and they are cleared rapidly from the plasma at about 8 or 9 days post infusion (Richter 1999, Drug Met. Disp. 27, 21-25).

Canine Model of Inflammation

All experiments were carried out with prior approval of the Institutional Ethics Committee (CRL, Ireland). Beagle dogs were injected (=day −1) with kaolin into the footpad of one hind leg in order to generate a self-resolving inflammation beginning approximately 24 hours later and which causes the dogs to become temporarily lame. In this model, once the initial inflammation response to kaolin recedes, the dogs become steadily less lame over the period of approximately 1-2 weeks and then make a full recovery.

Groups of 3 dogs were injected intravenously with either anti-canine (HCA isotype) NGF monoclonal antibodies at 200 µg/kg body weight or phosphate buffered saline as vehicle control (=day 0). The dogs were assessed for lameness over 7 days by a visual scoring method (score 0, no lameness (full weight bearing); score 1, slight lameness (not full weight bearing but walking well); score 2, moderate lameness (slightly weight bearing and not walking well), score 3, severe lameness (not weight bearing)). Observers were blinded to which dogs received which injection.

Figure 10:
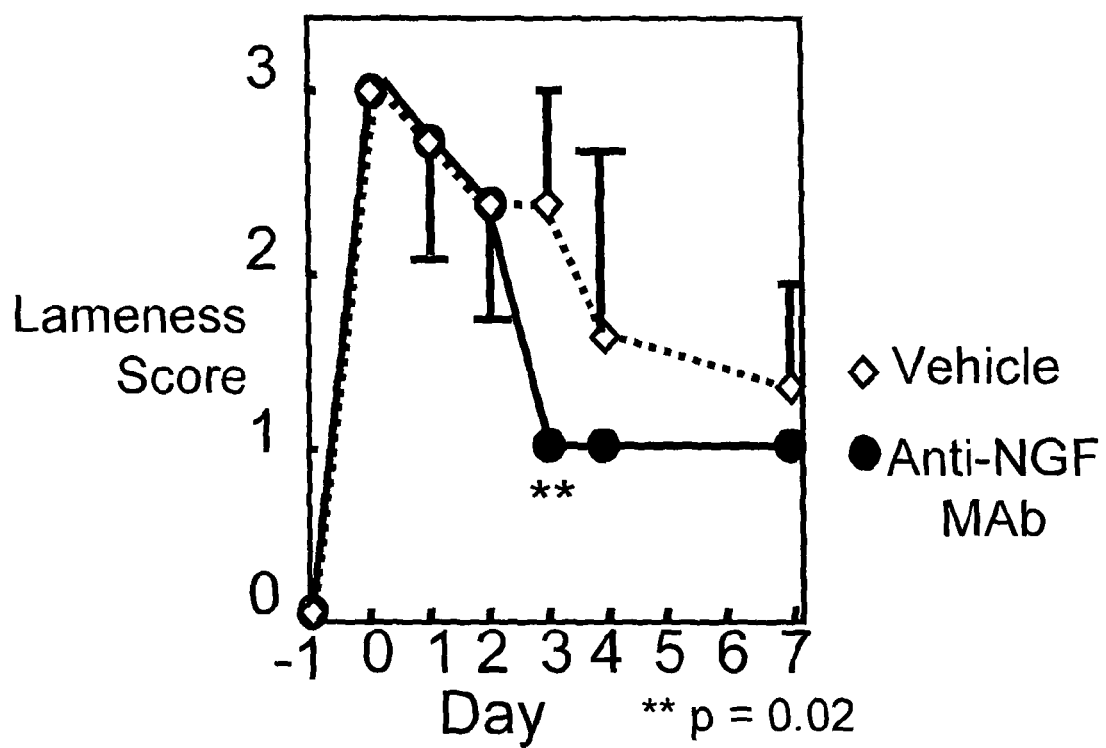
FIG. 10 shows that anti-canine NGF monoclonal antibodies (HCA isotype, purified by Method I) reduce inflammatory pain in dogs. Kaolin was injected into the footpad of beagle dogs at Day −1, antibody or vehicle control at Day 0 and lameness was measured by a visual scoring scale.

The results are shown in FIG. 10. Lameness scores were reduced in the dogs receiving anti-NGF monoclonal antibodies by day 3 post-injection compared with vehicle control, indicating that the anti-NGF monoclonal antibodies had an effect in reducing the pain in the dogs over that seen with vehicle alone. The delayed activity is consistent with the plasma pharmacokinetics of anti-canine NGF monoclonal antibodies which demonstrated a slow tissue distribution (alpha) phase of approximately 30 hours and the relatively poor vascularisation of the footpad area. The results shown in FIG. 10 show that the anti-canine NGF antibodies of the present invention reduce inflammatory pain in dogs with a consequent reduction in lameness.

Together the results described by this inventor demonstrate that purified canine antibodies constructed using the CDC inactive HCA isotype are safe and effective in canines and have a desirable long half-life.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

DEFINITIONS

Unless otherwise defined, all technical and scientific terms used herein have the meaning commonly understood by a person who is skilled in the art in the field of the present invention. The meaning and scope of the terms should be clear, however, in the event of any ambiguity, definitions provided herein take precedent over any dictionary or extrinsic definition.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

As used herein, terms such as "a", an and the include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like. Further, unless otherwise required by context, singular terms shall include pluralities and plural terms shall include the singular.

As herein defined, the term "pain" means an unpleasant sensory and emotional experience associated with actual or potential tissue damage, or described in terms of such damage.

In relation to operative or post-operative pain, the US Animal Welfare Act (Animal Welfare Act 2002. AWA regulations, CFR, Title 9 (Animals and Animal Products), Chapter 1 (Animal and Plant Health Inspection Service, Department of Agriculture). Subchapter A (Animal Welfare), Parts 1-4) defines a painful procedure as any procedure that would reasonably be expected to cause more than slight or momentary pain or distress in a human being to which that procedure was applied, that is, pain in excess of that caused by injections or other minor procedures. Therefore, if a canine undergoes a painful surgical procedure, the animal should receive postoperative analgesics.

In further instance, a canine may be experiencing significant or chronic pain as a result of an associated medical condition such as rheumatoid arthritis, osteoarthritis, inflammation or a cancerous or malignant condition.

The term "nociception" refers to the perception of noxious stimuli. As herein defined "neuropathic pain" (also known as 'neuralgia') is a pain that comes from problems with signals from the nerves. It may arise as a consequence of a lesion or disease affecting the somatosensory system. There are causes of neuropathic pain and it may be associated with abnormal sensations called dysesthesia, which occur spontaneously. Alternatively, it may be associated with allodynia which results when the pain comes on, or gets worse, with a touch or stimulus that would not normally cause pain. For example, a slight touch on the face may trigger pain if you have trigeminal neuralgia, or the pressure of the bedclothes may trigger pain if you have diabetic neuropathy. Neuropathic pain may also result from allodynia, where the pain comes on, or gets worse, with a touch or stimulus that would not normally cause pain. For example, a slight touch to the face may trigger pain if a subject has trigeminal neuralgia. Neuropathic pain relating to hyperalgesia means that severe pain results from a stimulus or touch that would normally cause only slight discomfort, while paraesthesia means that uncomfortable or painful feelings occur even when there is nothing in contact with the area causing the pain, for example pins and needles. Other forms of neuropathic pain involve pruritis or itch, which can be associated with allergic or inflammatory responses in the skin and inflammatory pain resulting from tissue damage and repair processes As defined herein, the term "NGF neutralising antibody" or similar describes an antibody that is capable of neutralising the biological activation and signalling of NGF. The neutralising antibody, which may also be referred to as an antagonistic antibody, or a blocking antibody, specifically, and preferably selectively, binds to NGF and inhibits one or more biological activities of NGF. For example, the neutralising antibody may inhibit the binding of a NGF to its target ligand, such as the cell membrane bound TrkA or p75 receptors.

As used herein, the term "biological activity" refers to any one or more inherent biological properties of a molecule (whether present naturally as found in vivo, or provided or enabled by recombinant means). Biological properties include but are not limited to receptor binding and/or activation; induction of cell signalling or cell proliferation, inhibiting cell growth, induction of cytokine or chemokine production, induction of apoptosis, and enzymatic activity.

The term "complementarity determining region (CDR)", as used herein, refers to amino acid sequences which together define the binding affinity and specificity of the natural Fv region of a native immunoglobulin binding site as delineated by Kabat et al. (Kabat, E. A., Wu, T. T., Perry, H., Gottesman, K. and Foeller, C. (1991) Sequences of Proteins of Immunological Interest, Fifth Edition. NIH Publication No. 91-3242). The term "framework region (FR)", as used herein, refers to amino acid sequences interposed between CDRs. These portions of the antibody serve to hold the CDRs in appropriate orientation (allows for CDRs to bind antigen).

The term "constant region (CR)" as used herein, refers to the portion of the antibody molecule which confers effector functions. In the present invention, constant regions typically mean canine constant regions, that is that the constant regions of the subject canininsed antibodies are derived from canine immunoglobulins.

The term "chimeric antibody" as used herein refers to an antibody containing sequences derived from two different antibodies, which typically are of different species. Most typically chimeric antibodies comprise variable domains derived from a donor specifies which bind specifically to a target epitope and constant domains derived from antibodies obtained from the target species to whom the antibody is to be administered.

The term "immunogenicity" as used herein refers to a measure of the ability of a targeting protein or therapeutic moiety to elicit an immune response (humoral or cellular) when administered to a recipient. The present invention is concerned with the immunogenicity of the subject caninised antibodies. Preferably the antibodies of the present invention have no immunogenicity, that is that no neutralising antibodies will be raised against them when administered to a canine, and further, no effector functions are mediated by the Fc regions of the antibody.

The term "identity" or "sequence identity" as used herein, means that at any particular amino acid residue position in an aligned sequence, the amino acid residue is identical between the aligned sequences. The term "similarity" or "sequence similarity" as used herein, indicates that, at any particular position in the aligned sequences, the amino acid residue is of a similar type between the sequences. For example, leucine may be substituted for an isoleucine or valine residue. This may be referred to as conservative substitution. Preferably when the amino acid sequences of the invention are modified by way of conservative substitution of any of the amino acid residues contained therein, these changes have no effect on the binding specificity or functional activity of the resulting antibody when compared to the unmodified antibody.

Sequence identity with respect to a (native) polypeptide of the invention and its functional derivative relates to the percentage of amino acid residues in the candidate sequence which are identical with the residues of the corresponding native polypeptide, after aligning the sequences and introducing gaps, if necessary, to achieve the maximum percentage homology, and not considering any conservative substitutions as part of the sequence identity. Neither N- or C-terminal extensions, nor insertions shall be construed as reducing sequence identity or homology. Methods and computer programs for performing an alignment of two or more amino acid sequences and determining their sequence identity or homology are well known to the person skilled in the art. For example, the percentage of identity or similarity of 2 amino acid sequences can be readily calculated using algorithms e.g. BLAST (Altschul et al. 1990), FASTA (Pearson & Lipman 1988), or the Smith-Waterman algorithm (Smith & Waterman 1981).

As used herein, reference to an amino acid residue having the "highest homology" to a second amino acid residue refers to the amino acid residue which has the most characteristics or properties in common with the second amino acid residue. In determining whether an amino acid residue has the highest homology to a second amino acid residue, an assessment may typically be made of factors such as, but not limited to, charge, polarity, hydrophobicity, side arm mass and side arm dimension.

The term "corresponding position" as used herein to refer to an amino acid residue that is present in a second sequence at a position corresponding to a specified amino acid residue in a first sequence is intended to refer to the position in the second sequence which is the same position as the position in the first sequence when the two sequences are aligned to allow for maximum sequence identity between the two sequences. Amino acid residues at corresponding positions have the same Kabat numbering.

The term "consists essentially of" or "consisting essentially of" as used herein means that a polypeptide may have additional features or elements beyond those described provided that such additional features or elements do not materially affect the ability of the antibody or antibody fragment to have binding specificity to canine NGF. That is, the antibody or antibody fragments comprising the polypeptides may have additional features or elements that do not interfere with the ability of the antibody or antibody fragments to bind to canine NGF and antagonise canine NGF functional activity. Such modifications may be introduced into the amino acid sequence in order to reduce the immunogenicity of the antibody. For example, a polypeptide consisting essentially of a specified sequence may contain one, two, three, four, five or more additional, deleted or substituted amino acids, at either end or at both ends of the sequence provided that these amino acids do not interfere with, inhibit, block or interrupt the role of the antibody or fragment in binding to canine NGF and sequestering its biological function. Similarly, a polypeptide molecule which contributes to the canine NGF antagonistic antibodies of the invention may be chemically modified with one or more functional groups provided that such functional groups do not interfere with the ability of the antibody or antibody fragment to bind to canine NGF and antagonise its function.

As used herein, the term "effective amount" or "therapeutically effective amount" means the amount of an agent, binding compound, small molecule, fusion protein or peptidomimetic of the invention which is required to deliver the required therapeutic effect.

The terms "polypeptide", "peptide", or "protein" are used interchangeably herein to designate a linear series of amino acid residues connected one to the other by peptide bonds between the alpha-amino and carboxy groups of adjacent residues. The amino acid residues are usually in the natural "L" isomeric form. However, residues in the "D" isomeric form can be substituted for any L-amino acid residue, as long as the desired functional property is retained by the polypeptide.

As herein defined an "antibody" encompasses antigen-binding proteins which specifically bind to a target antigen of interest, in this case canine nerve growth factor, having one or more polypeptides that can be recombinantly prepared or which are genetically encodable by immunoglobulin genes, or fragments of immunoglobulin genes. The term "antibody" encompasses monoclonal and chimeric antibodies, in particular caninised antibodies, and further encompasses polyclonal antibodies or antibodies of any class or subtype. An "antibody" further extends to hybrid antibodies, bispecific antibodies, heteroantibodies and to functional fragments thereof which retain antigen binding.

The phrase "specifically binds to" refers to the binding of an antibody to a specific protein or target which is present amongst a heterogeneous population of proteins. Hence, when present in specific immunoassay conditions, the antibodies bind to a particular protein, in this case canine NGF, and do not bind in a significant amount to other proteins present in the sample.

As defined herein, a "canine" may also be referred to as a "dog". Canines can be categorised as belonging to the subspecies with the trinomial name *Canis lupus* familiaris (*Canis familiaris domesticus*) or *Canis lupus* dingo. Canines include any species of dog and includes both feral and pet varieties, the latter also being referred to as companion animals.

The present invention will now be described with reference to the following examples which are provided for the purpose of illustration and are not intended to be construed as being limiting on the present invention. The methods and techniques of the present invention are generally performed according to conventional methods well known in the art and as described in various general and more specific references that are cited and discussed throughout the present specification unless otherwise indicated.

EXAMPLES

Example 1

Design and Production of Anti-Canine NGF Antibodies Having Different Canine Isotypes Antibodies directed to canine NGF (termed caN antibodies) were designed and constructed using identical variable heavy domains (VH) joined to heavy chain constant domains (CH2 and CH3) selected from HCA (SEQ ID NO:1), HCB (SEQ ID NO:2), HCC (SEQ ID NO:3) or HCD (SEQ ID NO:4). A variable light chain (VL) was joined to the canine kappa constant domain (SEQ ID NO:5). The combined amino acid sequences were converted to expressible form in mammalian cells by the optimal selection of codons and full chemical gene synthesis and cloning into a mammalian cell expression vector pcDNA3.1+. Specifically, the designed amino acid sequences were constructed into synthetic cDNA-expressible form and cloned into a mammalian cell expression vector pcDNA3.1(+). Whole antibody sequences were produced by combining caninised variable domain sequences with C-terminal canine constant heavy or constant light chain sequences. The caninised aD11 VH domain was combined with each of the four heavy chain isotypes HCA, HCB, HCC and HCD (SEQ ID NO:1-SEQ ID NO:4) and the caninised aD11 VL domain with the canine kappa light chain constant domain (SEQ ID NO:5). The combined amino acid sequences were converted to expressible form in mammalian cells by the optimal selection of codons and full chemical gene synthesis and cloning into a mammalian cell expression vector pcDNA3.1+.

Figure 1:
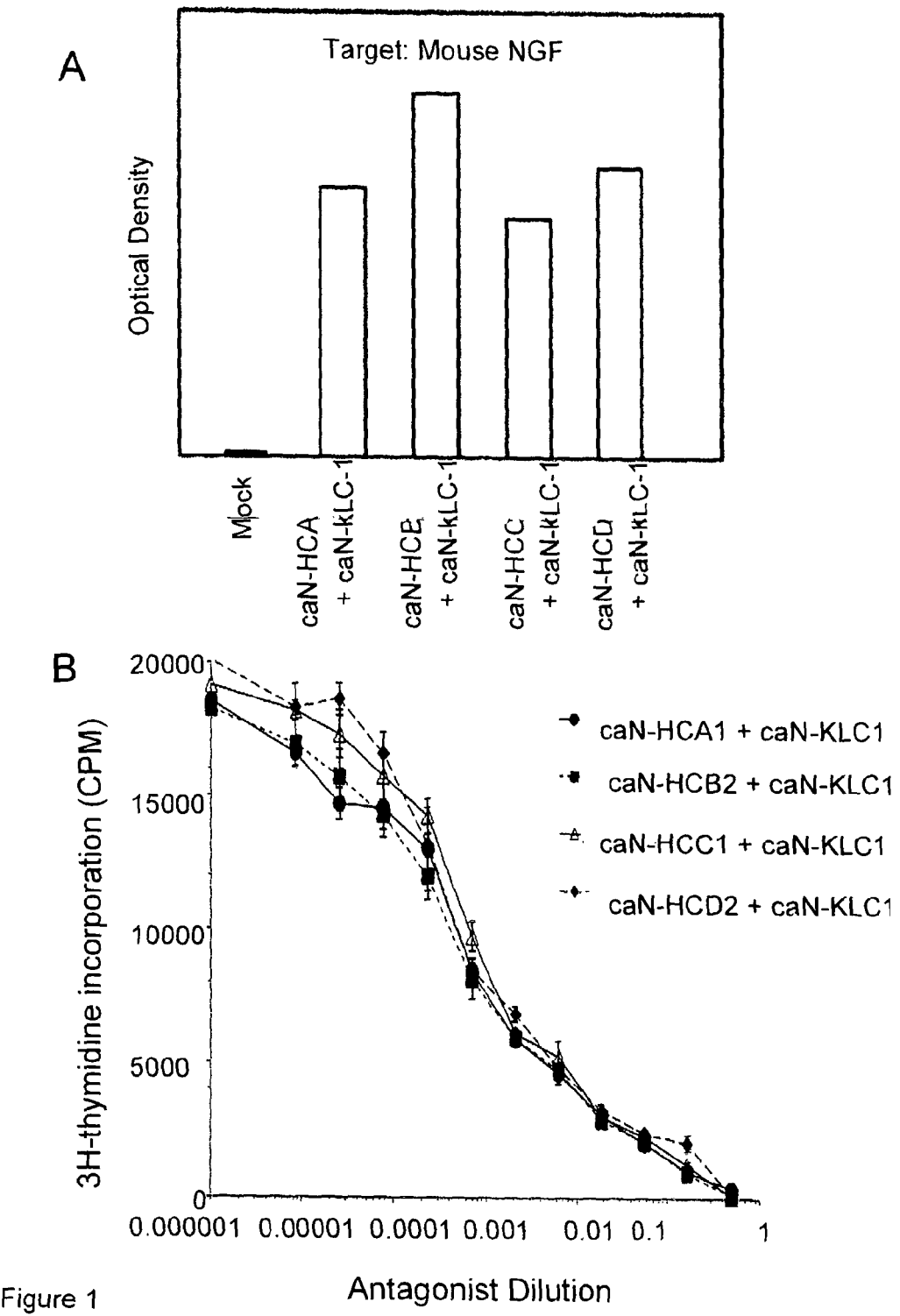
FIGS. 1A and 1B show equivalent binding of anti-NGF antibodies (expressed into the supernatant of transfected CHO cells) constructed using four different isotypes of canine heavy chains (HCA, HCB, HCC, HCD) to murine NGF by ELISA (FIG. 1A) and equivalent inhibition of NGF proliferation of TF-1 cells (FIG. 1B).

Combinations of caninised heavy and light chain cDNA plasmids (caN-HCA-kLC using SEQ ID NO:5 plus SEQ ID NO:1 (HCA); caN-HCB-kLC using SEQ ID NO:5 plus SEQ ID NO:2 (HCB); caN-HCC-kLC using SEQ ID NO:5 plus SEQ ID NO:3 (HCC) and caN-HCD-kLC using SEQ ID NO:5 plus SEQ ID NO:4 (HCD)) were transfected into CHO cells, the supernatants harvested and reacted in ELISA format with NGF. Following incubation and wash steps, the bound canine antibody was detected by reactivity with a goat-anti canine IgG specific polyclonal antibody linked to horseradish peroxidase (HRP) and developed using TMB. The optical density of the resulting product was measured at 450 nm and compared with that from mock empty vector transfected supernatant. The results of binding to NGF for the 4 caninised antibody isotypes are shown in FIG. 1. Each of these antibodies has the same light chain (caN-kLC), this being a light chain comprising a canine kappa constant domain. Each antibody has a different heavy chain constant domain. Accordingly a specific heavy chain variable domain is combined with one of 4 different constant domains (caN-HCA, caN-HCB, caN-HCC or caN-HCD). Equivalent binding to NGF was observed for each of the canine heavy chain isotypes.

Antibody supernatants were tested for NGF binding by ELISA assay (FIG. 1A) and NGF neutralisation by TF-1 cell proliferation inhibition assay (FIG. 1B). As can be seen in FIG. 1, the four isotypes had equivalent activity to one another in these assays, that is, they all bound specifically to canine NGF.

Example 2

Complement Deposition Induced by NGF-Captured Caninised Antibodies

The four antibody-containing supernatants were then assessed for their ability to bind complement when bound to NGF using a complement C1q ELISA. Plates were coated with 100 μl/well of 5 μg/ml mouse NGF and blocked with 5% BSA/PBS. Coated wells were incubated for 1 hour at room temperature with cell culture supernatants, containing recombinant caninised anti-NGF IgG isotypes, diluted in PBS/1% BSA (100 μl/well). The plates were washed and incubated for 1 hour at room temperature with 100 μl/well of human serum diluted 1/100 in veronal buffered saline containing 0.5 mM $MgCl_2$, 2 mM $CaCl_2$, 0.05% Tween-20, 0.1% gelatin and 0.5% BSA. After washing, plates were incubated with 100 μl of a 1/800 dilution of sheep anti-C1q-HRP (Serotec) in PBS/1% BSA. After washing, plates were developed by the addition of 100 μl TMB substrate. All complement C1q binding expressed as A450 minus heat-inactivated complement background. Development was stopped by the addition of 100 μl of 2N $H_2SO_4$ and absorbance read at 450 nm.

Figure 2:
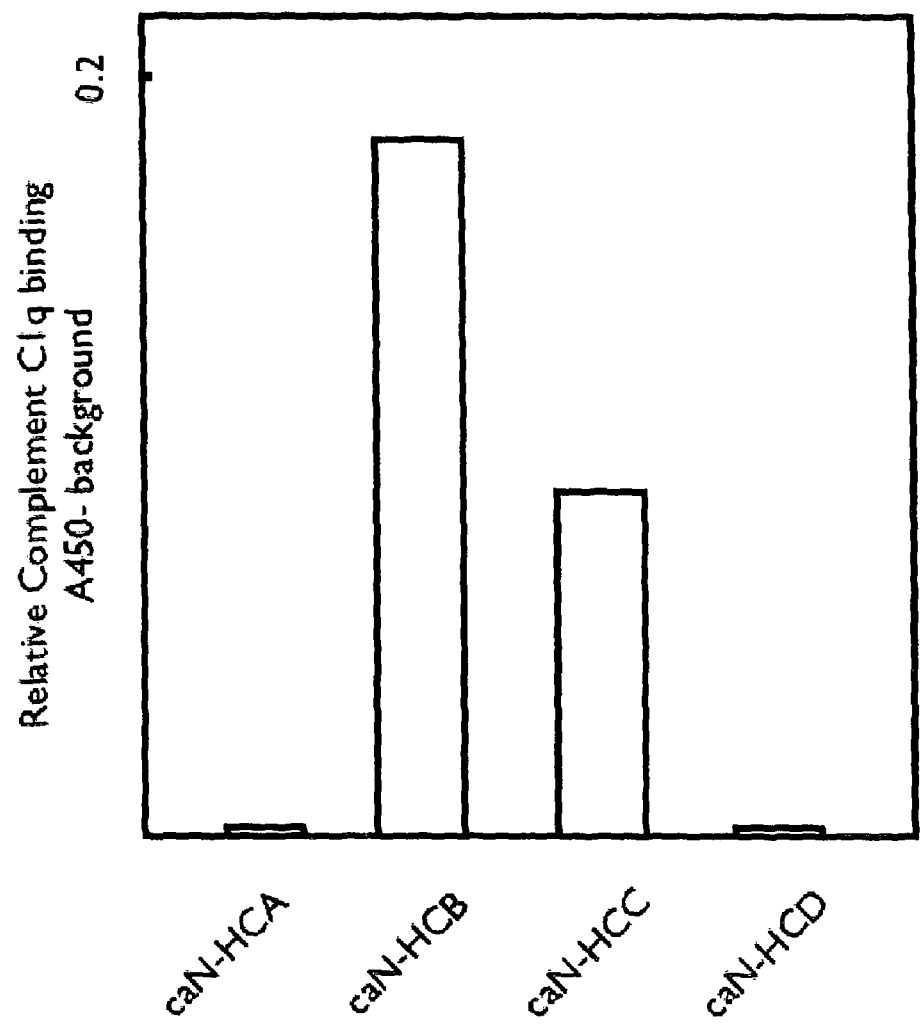
FIG. 2 shows differential binding of complement to NGF-bound anti-canine NGF antibody isotypes as measured by anti-C1q ELISA.

The results are shown in FIG. 2. These results show binding of C1q to immobilised caninised HCB and HCC type antibodies and no binding of C1q to caninised HCA and HCD type antibodies. Hence, the results surprisingly indicate that different canine derived heavy chains exhibit different complement binding and hence activation characteristics and that the caninised antibodies with type HCA and HCD heavy chains unexpectedly are preferable for use in antagonising canine NGF. Accordingly, the ability to produce an antibody which binds specifically to canine NGF, yet which does not mediate CDC is highly advantageous, as an antibody which binds specifically to NGF, yet which mediated an immune response in proximity to the cells expressing NGF, would be highly undesirable.

Example 3

Figure 3A:
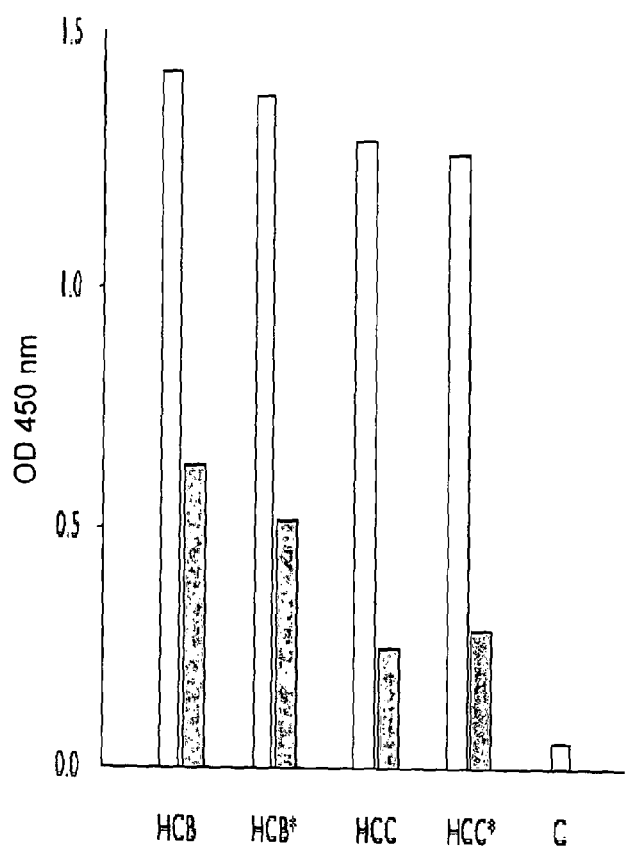
FIGS. 3a and 3b show binding of NGF-captured glycosylated and aglycosylated caninised anti-NGF monoclonal antibodies to complement as measured by anti-C1q ELISA.
Figure 3B:
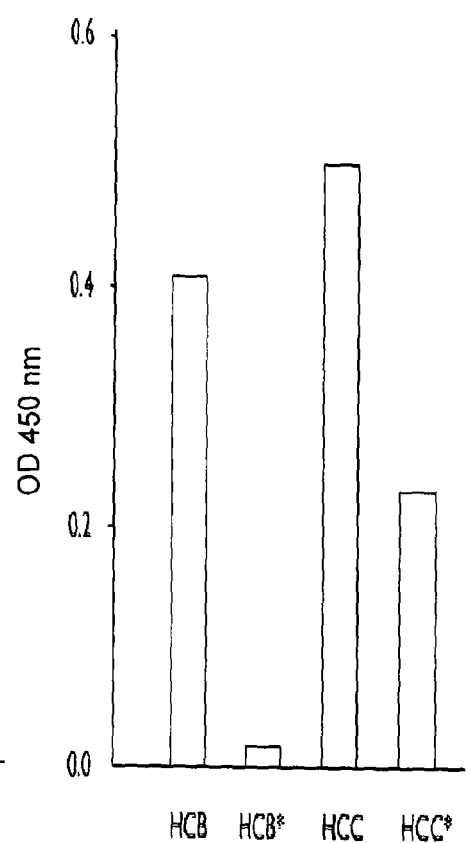

Complement Binding of NGF Captured N-Glycosylated and Aglycosyl Variants of Anti-Canine-NGF Monoclonal Antibodies with HCB and HCC Heavy Chain Isotypes A comparison of the binding of N-glycosylated and aglycosyl variants of anti-canine-NGF monoclonal antibodies to NGF with HCB and HCC heavy chain isotypes was carried out. Expression vectors encoding the light and heavy chain pairs described by SEQ ID NO:5 and SEQ ID NO:2 (HCB), SEQ ID NO:5 and SEQ ID NO:6 (HCB*), SEQ ID NO:5 and SEQ ID NO:3 (HCC), or SEQ ID NO:5 and SEQ ID NO:7 (HCC*) were co-transfected into CHO cells and the supernatants compared by binding ELISA to mouse NGF. The results are shown in FIG. 3. The left hand panel shows detection by ELISA of expression of anti-NGF MAbs constructed with HCB heavy chain (HCB), aglycosyl HCB heavy chain (HCB*), HCC heavy chain (HCC) or aglycosyl HCC heavy chain (HCC*)—the open bars show undiluted supernatant, the shaded bars ⅒ diluted supernatant and C shows an undiluted negative control supernatant. Equivalent binding to NGF was observed.

Similarly, antibodies designed to remove the constant domain N-linked glycosylation site of HCB and HCC (referred to as HCB* (SEQ ID NO: 6) and HCC* (SEQ ID NO:7)) were co-expressed with light chain and assessed for complement activity (FIG. 3) in an attempt to ablate their complement binding. Surprisingly, the aglycosylated HCB* was not capable of binding complement, however the aglycosylated HCC* remained capable of binding complement. The identification of canine derived glycosylated and aglycosylated heavy chains which do not mediate complement fixing is a particularly advantageous finding as NGF is a soluble mediator involved in nociception.

CHO cell transfectant supernatants from were tested for their ability to recruit complement using the C1q ELISA assay described in Example 2. The results are shown in FIG. 3—right hand panel. Together the results in FIG. 3 demonstrate that the ability to recruit complement C1q was abolished by removal of the N-linked glycosylation site in the B type heavy chain (HCB*) and was diminished by a similar mutation in the C type heavy chain (HCC*).

Accordingly, it is shown herein, quite surprisingly, that where an antibody has a canine-derived heavy chain of the HCA, HCD subtype or aglycosylated HCB* isotype, the binding of the antibody to canine NGF does not result in complement activation (and potentially other downstream effector functions, such as ADCC and ADCP). Hence, said antibodies, in antagonising the biological functional activity of a target, such as canine NGF, by preventing binding of canine NGF to cell membrane bound TrkA or p75 receptors, inhibit the associated downstream intracellular signalling cascade. Furthermore, as NGF expression frequently occurs in the proximity of nerves, such NGF antagonising or neutralising antibodies, which have canine derived heavy chain of the HCA, HCD or HCB* subtype, sequester canine NGF biological activity without recruiting a wider immune response. Hence, the results surprisingly indicate that different canine derived heavy chains exhibit different complement binding and activation characteristics and that the caninised antibodies with type HCA and HCD heavy chains have been unexpectedly shown to be preferable for use in antagonising canine NGF. The identification of canine derived heavy chains which do not mediate complement fixing is a particularly advantageous finding as NGF is a soluble mediator. Such functional properties are both unexpected and highly desirable.

Example 4

Figure 4:
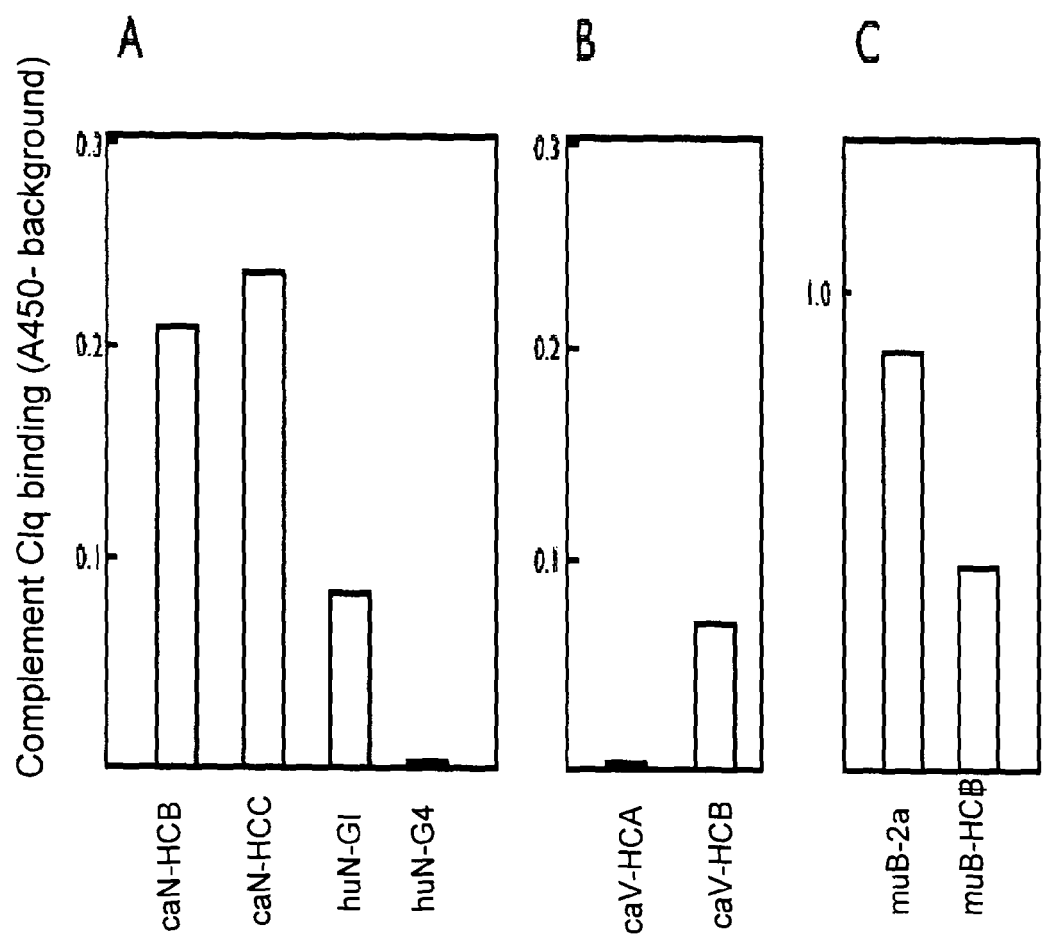
FIG. 4 shows the binding of NGF-captured caninised anti-NGF monoclonal antibodies (MAbs), anti-canine VEGF MAbs and anti-human CD20/canine HCB chimeric MAb to complement measured by anti-C1q ELISA. In particular.

Production of Antibodies with Canine Heavy Chain Constant Domains to Other Antigens: VEGF and CD20 and their Binding to Complement Given the surprising result that different canine heavy chain isotypes have differential binding to complement, anti-VEGF and anti-CD20 antibodies were similarly constructed using canine heavy chain constant domains expressed in CHO cells using the same methodology as described in Example 1. Assay results from these antibody supernatants in the complement ELISA are shown in FIG. 4. The results compared to the anti-NGF antibodies described above for their ability to recruit complement following binding to their cognate antigen.

The results are shown in FIG. 4. Panel A shows that caninised anti-NGF MAb constructed using canine heavy chain isotypes B and C and humanised antibodies constructed using human heavy chain isotypes IgG1 and IgG4 were captured onto NGF coated plates, incubated with human serum and bound C1q was detected by ELISA using anti-C1q polyclonal antibodies conjugated to HRP. Panel B shows the results of complement C1q binding to VEGF-captured caninised anti-VEGF MAbs constructed using canine heavy chain isotypes A and B (SEQ ID NO:8, SEQ ID NO:9). Panel C shows the results of complement C1q binding to anti-CD20 MAb captured on huCD20 extracellular domain peptide (muB-2a: murine anti-human CD20 MAb and muB-HCB: murine anti-human CD20 MAb expressed as a chimeric fusion protein with canine heavy chain isotype B (SEQ ID NO:9). All complement C1q binding expressed as A450 minus heat-inactivated complement background.

Together these data show that anti-VEGF antibodies constructed using HCB but not HCA canine heavy chain constant domains could recruit complement and an anti-CD20 antibody constructed using canine HCB could bind complement and so parallel the differential binding of anti-NGF antibody isotypes to complement described above. In summary, these data support the surprising observation that antigen-captured antibodies constructed with HCB and HCC isotypes bind complement whereas HCA and HCD do not. The identification that HCB and HCC isotypes bind complement is particularly advantageous for tumour cell killing e.g. of VEGF-expressing or CD20 expressing tumour cells.

The results of these experiments support the unexpected finding from Example 1 that antibodies comprising canine heavy chain constant domain HCA, HCD and aglycosylated HCB (HCB*) isotypes result in immunoglobulins which do not mediate CDC activity. Accordingly, the inventor has identified for the first time that such canine derived heavy chains have utility in immunoglobulins for use in therapeutic methods where a CDC mediated immune response is not desired. Examples of such uses may be found in the inhibition by canine immunoglobulins of cytokines or chemokines, growth factors, hormones and other extracellular mediators including complement itself in vivo or in diseases such as pain, macular degeneration or inflammation.

While the HCA, HCD and HCB* isotypes are most useful for design of CDC inactive antibodies, the inventor has also surprisingly identified that canine antibodies of HCB (calgG-B) and HCC (calgG-C) isotypes are useful in the design of CDC active antibodies. Such antibodies are useful when targeting cells for destruction, for example in cancer therapy. There are many human tumour antigens that are targeted using CDC active antibodies, including CD20, HER2 and the EGFR so canine antibodies constructed using HCB and HCC isotypes will have parallel uses in canines.

Example 5

Purification of Anti-NGF Monoclonal Antibodies Following Expression in CHO Cells Since canine anti-NGF monoclonal antibodies of the HCA and HCD isotypes have desirable lack of binding to complement (FIG. 2), but bind weakly to *Staphylococcus* Protein A (FIG. 5), alternative methods of purification were developed (FIG. 6). Anti-canine NGF monoclonal antibodies (constructed using heavy chain isotype HCA) were expressed in CHO cells and following extensive experimentation it was surprisingly found that the canine anti-NGF antibody could be fractionated to high purity (>89% monomeric IgG peak, as shown in FIGS. 6A, 6D) by two alternative purification methods.

Figure 6A:
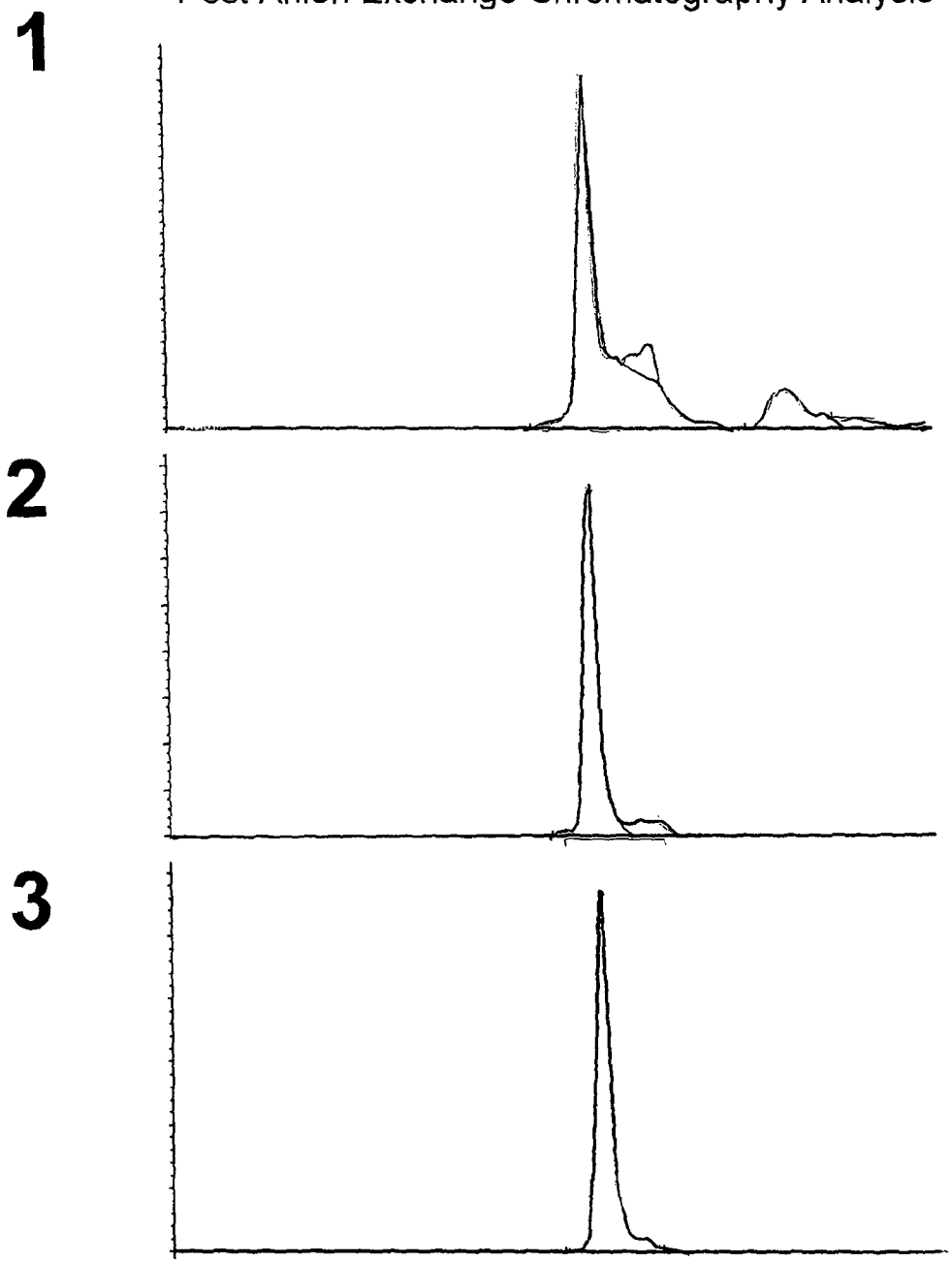
FIGS. 6A and 6B show the quantitative purification of anti-canine NGF antibody (HCA isotype) using a three-step method (Method I) comprising (1) anion exchange chromatography, (2) hydrophobic interaction chromatography and (3) size exclusion chromatography.
Figure 6B:
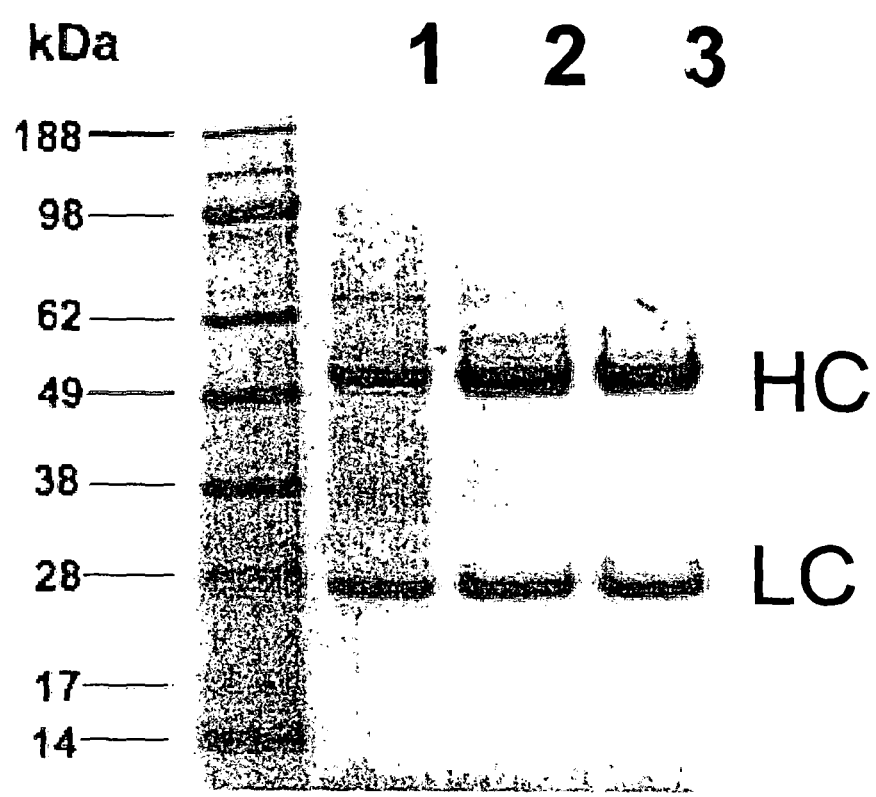
Figure 6C:
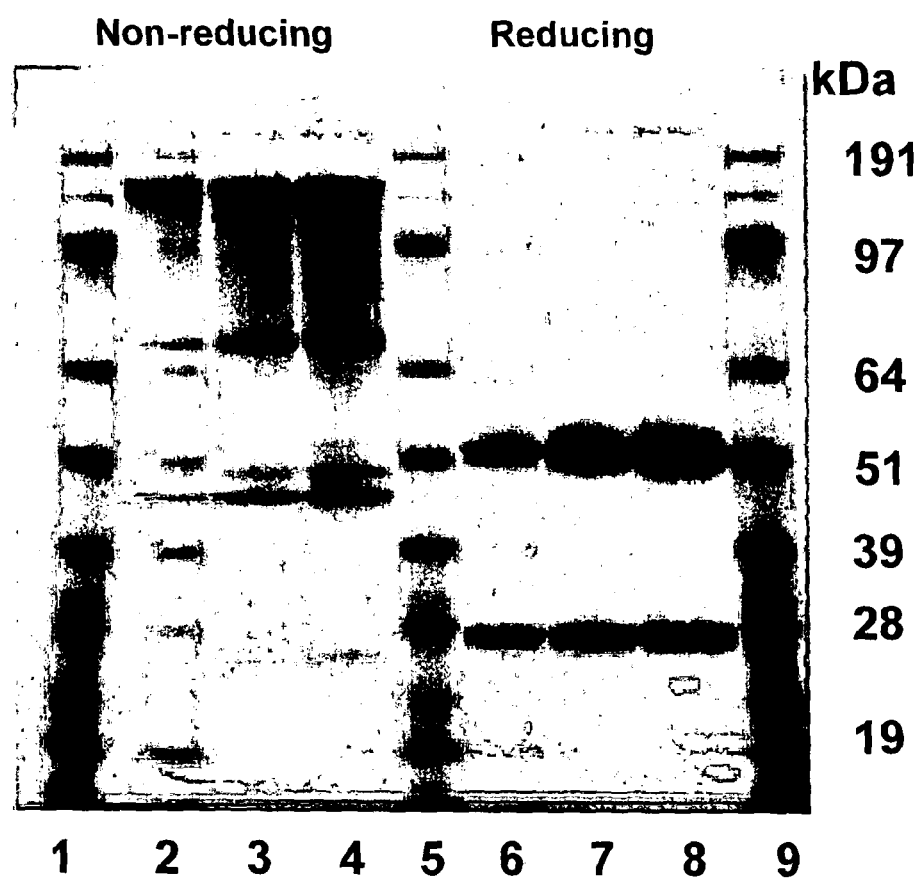
FIGS. 6C and D show the quantitative purification of the anti-canine NGF antibodies of the present invention using a two-step method (Method II) comprising Captoadhere chromatography and anion exchange chromatography.
Figure 6D:
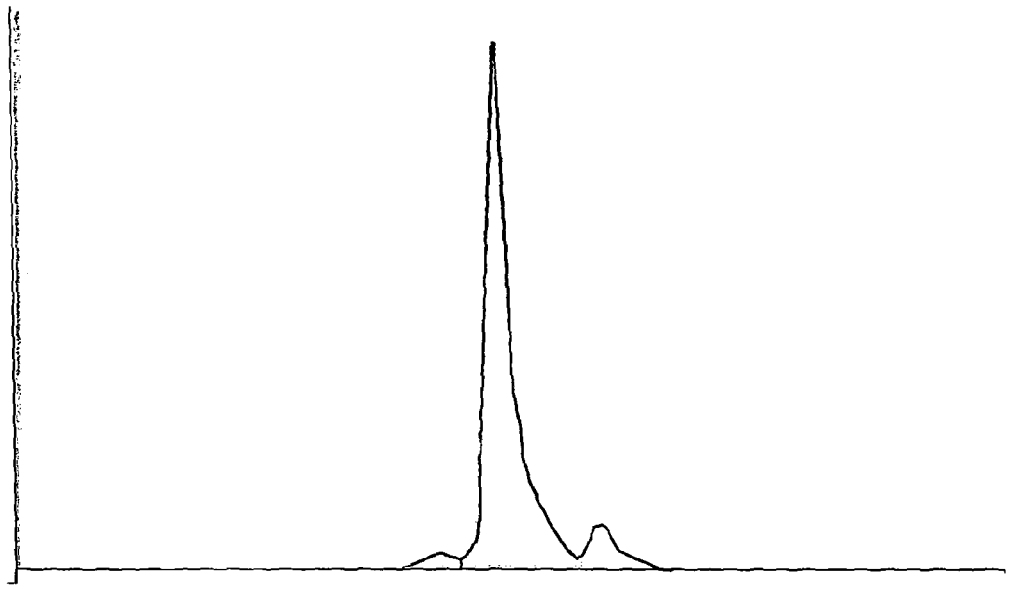
FIG. 6D: size exclusion chromatography of the purified anti-canine NGF antibody.
Figure 7B:
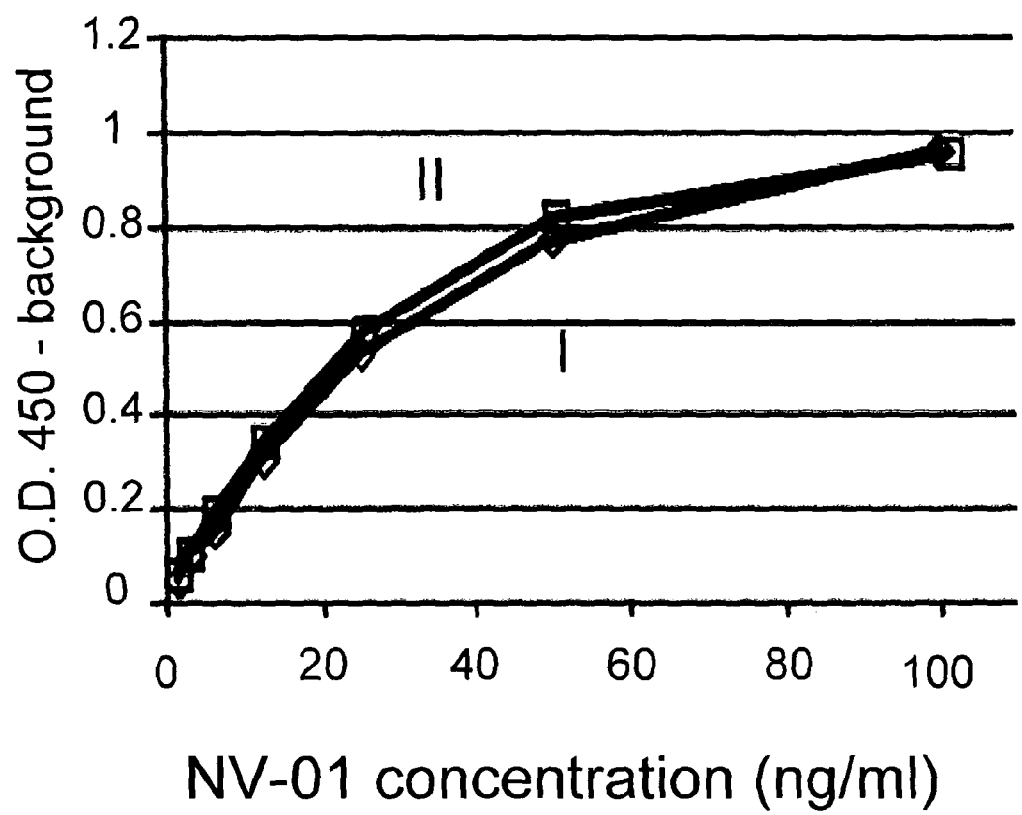
FIG. 7B: comparison by anti-NGF ELISA.

In the first method, anti-canine NGF monoclonal antibody was purified by anion exchange chromatography, hydrophobic interaction chromatography and size exclusion chromatography (Method I—FIGS. 6A and B). In the second method, the anti-NGF antibody could be purified by Captoadhere affinity chromatography followed by anion exchange chromatography (Method II—FIGS. 6C and D).

The main peak of anti-NGF monoclonal antibody purified by either method corresponds to a molecular weight of approximately 150 kDa. Comparison by SDS-PAGE and ELISA (FIG. 7) illustrates that Methods I and II produce antibody preparations with similar purity and bioactivity. Purified anti-NGF monoclonal antibodies produced by these methods were tested in the TF-1 NGF neutralisation assay (described in FIG. 1) and shown to have high potency (IC50 13 pM anti-NGF neutralised 37 pM NGF; not shown).

Example 6

Anti-Canine NGF Monoclonal Antibodies can be Safely Administered Intravenously to Canines and do not Cause Pyrexia Anti-canine NGF monoclonal antibodies derived from expression vectors containing canine HCA type heavy chain were expressed in CHO cells and purified by a combination of ion exchange chromatography, hydrophobic interaction chromatography and size exclusion chromatography (Method I, FIGS. 6A and B) and buffer exchanged into phosphate buffered saline. The antibodies were injected intravenously into beagle dogs at 2 mg/kg body weight and assessed for signs of toxicity by visual inspection by a veterinarian, change in body weight, body temperature and plasma biochemistry. FIG. 8 illustrates the body weight and temperature measurements. No changes were observed in these or any plasma biochemistry analyte measured (including sodium, potassium, chloride, calcium, phosphate, urea, creatinine, glucose, cholesterol, bilirubin, alanine transaminase, alkaline phosphatase, amylase, lipase, total protein or albumin: not shown).

Example 7

Plasma Pharmacokinetics of Anti-Canine (HCA Isotype) NGF Monoclonal Antibodies In-Vivo Demonstrates Long Serum Half-Life and Lack of Immunogenicity Anti-canine NGF monoclonal antibodies derived from expression vectors expressing canine HCA type heavy chain were expressed in CHO cells and purified by a combination of ion exchange chromatography, hydrophobic interaction chromatography and size exclusion chromatography and buffer exchanged into phosphate buffered saline (Method 1, FIGS. 6A and B). The antibodies were injected intravenously into beagle dogs at 2 mg/kg body weight and plasma samples were taken at various times over the following 2 weeks. Diluted plasma samples were assessed for anti-canine NGF antibody concentration by ELISA using NGF as target and anti-canine polyclonal antibody-horseradish peroxidase secondary reagent and developed as per FIG. 1. The results are shown in FIG. 9. The plasma concentrations measured were consistent with two-phase kinetics, with a tissue distribution (alpha) phase half-life of approximately 33 hours and surprisingly long elimination (beta) phase of approximately 9 days.

The absence of a sharp decline in plasma concentration of anti-canine NGF antibody concentration between 100 and 300 hours demonstrates that there are neither pre-existing neutralising antibodies to recombinant anti-NGF monoclonal antibodies in dog blood, nor were any such neutralising antibodies generated following infusion. By comparison, recombinant human immunoglobulin based proteins are neutralised by antibodies in dog blood at approximately 200 hours post infusion (Richter et al, Drug Metabolism and Disposition 27: 21, 1998). These results therefore show that anti-canine NGF antibodies of the present invention have a long serum half-life (approximately 9 days) in vivo following intravenous injection and that there are neither pre-existing antibodies nor newly generated antibodies that neutralise the injected anti-NGF antibodies over time.

Example 8

Effect of Anti-Canine NGF Monoclonal Antibodies in Reducing Inflammatory Pain In-Vivo Antibody Therapy:

Anti-canine NGF monoclonal antibodies derived from expression vectors including canine HCA type heavy chain were expressed in CHO cells and purified by a combination of ion exchange chromatography, hydrophobic interaction chromatography and size exclusion chromatography (Method I) and buffer exchanged into phosphate buffered saline.

Canine Model of Inflammation:

All experiments were carried out with prior approval of the Institutional Ethics Committee (CRL, Ireland). Beagle dogs were injected (=day −1) with kaolin into the footpad of one hind leg in order to generate a self-resolving inflammation beginning approximately 24 hours later and which causes the dogs to become temporarily lame. In this model, once the initial inflammation response to kaolin recedes, the dogs become steadily less lame over the period of approximately 1-2 weeks and then make a full recovery.

Groups of 3 dogs were injected intravenously with either anti-canine NGF monoclonal antibodies at 200 μg/kg body weight or phosphate buffered saline as vehicle control (=day 0). The dogs were assessed for lameness over 7 days by a visual scoring method (score 0, no lameness (full weight bearing); score 1, slight lameness (not full weight bearing but walking well); score 2, moderate lameness (slightly weight bearing and not walking well), score 3, severe lameness (not weight bearing)). Observers were blinded to which dogs received which injection.

The results are shown in FIG. 10. Lameness scores were reduced in the dogs receiving anti-NGF monoclonal antibodies by day 3 post-injection compared with vehicle control, indicating that the anti-NGF monoclonal antibodies had an effect in reducing the pain in the dogs over that seen with vehicle alone. The delayed activity is consistent with the plasma pharmacokinetics of anti-canine NGF monoclonal antibodies which demonstrated a slow tissue distribution (alpha) phase of approximately 30 hours and the relatively poor vascularisation of the footpad area. The results shown in FIG. 10 show that the anti-canine NGF antibodies of the present invention reduce inflammatory pain in dogs with a consequent reduction in lameness.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A method of treating a canine to neutralize a target antigen without inducing complement dependent cytotoxicity, comprising administering to a canine subject in need thereof a therapeutically effective amount of an antibody, fusion protein or antigen-binding fragment of an antibody that specifically binds the target antigen, wherein said antibody, fusion protein, or antigen-binding fragment comprises a heavy chain constant domain comprising the amino acid sequence of SEQ ID NO: 8, SEQ ID NO: 11; SEQ ID NO: 13, wherein the heavy chain constant domain does not bind C1q when the antibody, fusion protein, or antigen-binding fragment is bound to the target antigen.

2. The method as claimed in claim 1, wherein the method is for treating, inhibiting or ameliorating pain or inflammation in the canine subject.

3. The method as claimed in claim 2, wherein the pain is selected from the group consisting of neuropathic pain, oncologic pain, pain associated with, or resulting from, rheumatoid arthritis, pain associated with, or resulting from, osteoarthritis, pain associated with, or resulting from, inflammation and pain associated with, or resulting from, pruritis.

4. The method as claimed in claim 1, wherein the method minimizes activation of one or more downstream immune system effector functions selected from the group consisting of antibody dependent cell mediated cytotoxicity and antibody dependent cellular pathogenesis.

5. The method as claimed in claim 1, wherein the antibody, fusion protein or binding fragment has a heavy chain constant domain comprising the amino acid sequence of SEQ ID NO: 13.

6. A method of treating a canine to induce destruction of a target displaying a target antigen through complement dependent cytotoxicity, comprising administering to a canine subject in need thereof a therapeutically effective amount of an antibody, fusion protein or antigen-binding fragment of an antibody that that specifically binds the target antigen, wherein said antibody, fusion protein, or antigen-binding fragment comprises a heavy chain constant domain comprising the amino acid sequence of SEQ ID NO: 9, SEQ ID NO: 10; SEQ ID NO: 14, wherein the heavy chain constant domain binds C1q when the antibody, fusion protein, or antigen-binding fragment is bound to the target antigen.

7. The method as claimed in claim 6, wherein the method is for the treatment or prevention of a cancerous or malignant condition in the canine subject.

8. The method as claimed in claim 6, wherein the method mediates activation of one or more downstream immune system effector function selected from the group consisting of antibody dependent cell mediated cytotoxicity and antibody dependent cellular pathogenesis.

9. The method as claimed in claim 6, wherein the target antigen is a cancer specific antigen.

10. The method as claimed in claim 9, wherein the cancer specific antigen is selected from the group consisting of a cytokine, a chemokine, a growth factor, a cell surface receptor, a virus and a component of the complement cascade.

11. The method as claimed in claim 9, wherein the cancer specific antigen is selected from the group consisting of proteins CD2, CD4, CD8, CD20, EGFR, VEGFR and HER2.

* * * * *